(12) United States Patent
Godeau et al.

(10) Patent No.: US 7,119,896 B2
(45) Date of Patent: Oct. 10, 2006

(54) METHOD AND SYSTEM FOR MEASURING WEAR ON A TIRE

(75) Inventors: Gilles Godeau, Clermont-Ferrand (FR); Michel Robert, Cellule (FR); Georges Peyron, Riom (FR); Gilbert Menard, Volvic (FR)

(73) Assignee: Michelin Recherche et Technique S.A., Granges-Paccot (CH)

( * ) Notice: Subject to any disclaimer, the term of this patent is extended or adjusted under 35 U.S.C. 154(b) by 0 days.

(21) Appl. No.: 10/894,584

(22) Filed: Jul. 20, 2004

(65) Prior Publication Data

US 2005/0044943 A1    Mar. 3, 2005

(30) Foreign Application Priority Data

Jan. 21, 2002   (FR) .................................. 02 00850

(51) Int. Cl.
*G01N 21/88*      (2006.01)
(52) U.S. Cl. .................................. 356/237.2
(58) Field of Classification Search .. 356/237.1–237.6; 73/146.2–146.8, 146; 374/141, 143, 144
See application file for complete search history.

(56) References Cited

U.S. PATENT DOCUMENTS 3,648,164 A * 3/1972 Searle et al. ................ 324/639
4,884,434 A  12/1989 Satake et al.
6,067,159 A   5/2000 Discenzo et al.

FOREIGN PATENT DOCUMENTS

FR        2661373 A1 * 10/1991

OTHER PUBLICATIONS

Patent Abstracts of Japan. Pub. No. 11170819, Jun. 1999, Abstract of JP 09 345236.

* cited by examiner

*Primary Examiner*—Tu T. Nguyen
(74) *Attorney, Agent, or Firm*—Buchanan Ingersoll & Rooney PC

(57) ABSTRACT

The tread wear on a tire is measured while the tire is mounted on a wheel. Electromagnetic energy is transmitted to an internal space of the tire via a transmission element disposed in a tire tread element. That transmitted energy is detected inside the tire, and an energy variable from the detected electromagnetic radiation is determined which is used to determine a wear variable representative of wear on the tire tread element. A signal transmitter disposed within the internal space sends signals representative of the wear.

40 Claims, 11 Drawing Sheets

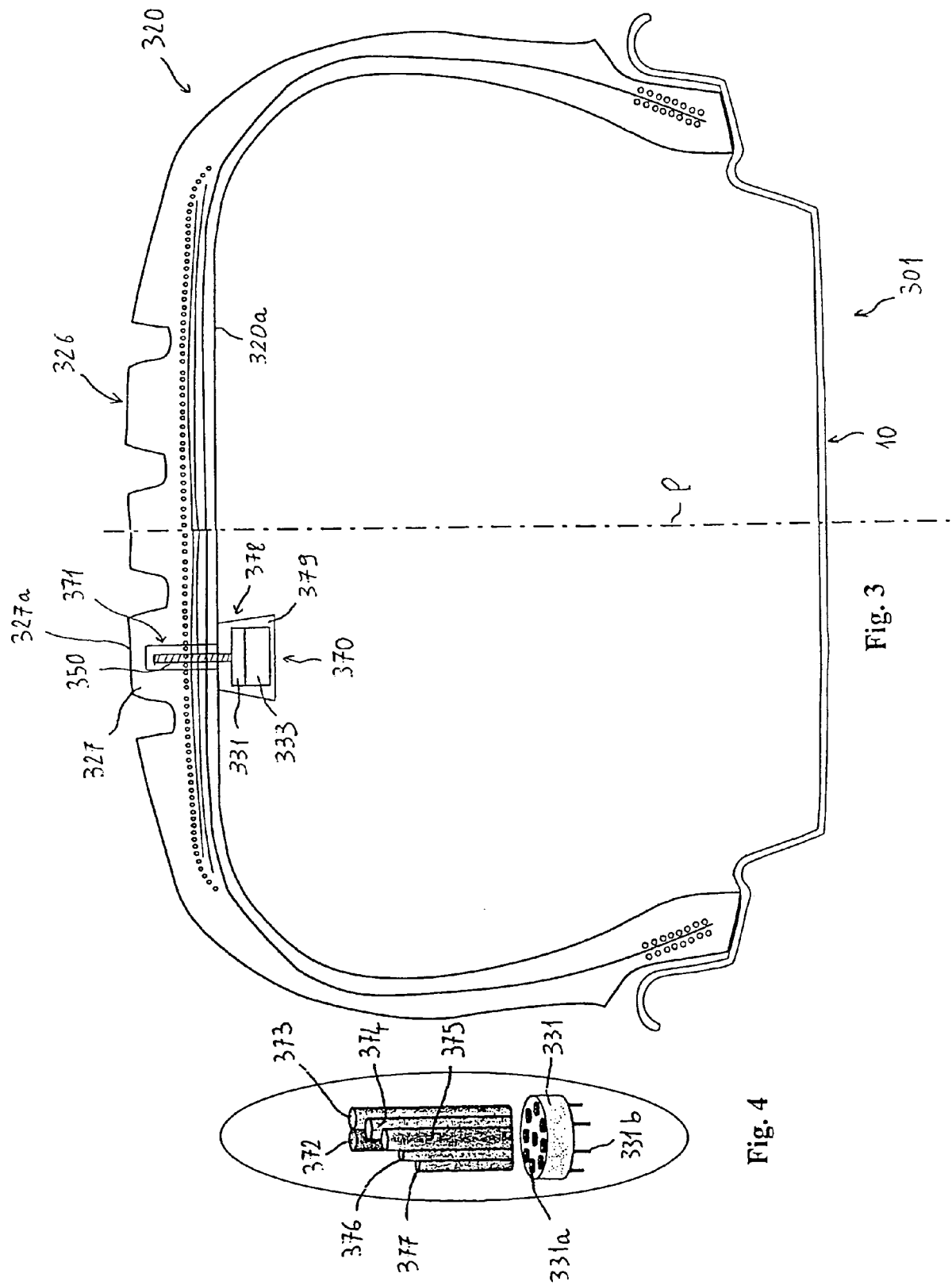

METHOD AND SYSTEM FOR MEASURING WEAR ON A TIRE

BACKGROUND AND SUMMARY OF THE INVENTION

The present invention concerns a method of measuring, the wear, when stopped or running, on at least one tire mounted on a wheel, a tire and a wheel provided separately for implementing this method, and a tire/wheel assembly for a motor vehicle comprising the tire and the wheel. The invention also concerns methods of manufacturing the tire and a motor vehicle comprising at least one such tire/wheel assembly.

It is known how to provide wear detectors on the tread pattern elements of a tire tread for motor vehicles.

The British patent publications GB-A-2 330 808 and GB-A-2 268 715 disclose visual wear detectors consisting of layers of colored rubber reflecting light, which are disposed over the entire circumference of the tire, in the mass of the tread, and which are visible following a given amount of wear on the tire.

A major drawback of these detectors lies in the precarious nature of the wear information obtained, which can only be noted visually and possibly much after the critical wear threshold of the tire has been exceeded.

One aim of the present invention is to propose a method of measuring the wear on at least one tire comprising tread pattern elements and mounted on a wheel, which makes it possible to remedy this drawback.

To this end, the wear measuring method according to the invention comprises the step of assigning a wear variable representing the wear on the element or elements to an energy variable representing the energy of electromagnetic radiation transmitted from the external space to the internal space of the or each tire through at least one of the elements.

Tread pattern element, in the present description, means any element in relief which is intended to be in contact at one time or another with the ground, i.e. as soon as running starts, or after wear on this element has begun. This element can thus consist of a block, for example substantially parallelepipedal or cylindrical in shape, or a circumferential rib with a variable transverse section (i.e. extending over all or part of the circumference of the tread).

It should be noted that the tread pattern element according to the invention can advantageously consist of a "wear indicator," for example in the form of a block or rib with a height substantially less than that of the tread patterns intended to be in contact with the ground during ground contact.

According to another characteristic of the invention, the energy variable itself represents the fact that an electromagnetic radiation transmission means is flush with the top surface of the top of the element, the top surface of the tread pattern elements being intended to be in contact with the ground right from the start or at a subsequent time during running.

According to another characteristic of the invention, the method comprises assigning, to a value of the energy variable less than at least one predetermined energy threshold, of a value of the wear variable corresponding to wear on the element which does not extend as far as at least one predetermined wear threshold.

According to one embodiment of the invention, the method comprises the allocation, to a value of the energy variable equal to or greater than the predetermined energy threshold, of a value of the wear variable corresponding to a wear on the element which has reached or exceeded the predetermined wear threshold.

According to another embodiment of the invention, the method comprises the allocation, to a plurality of values of the energy variable reaching or exceeding the predetermined energy threshold, of the same number of values of the wear variable corresponding respectively to levels of wear on the element reaching or exceeding the predetermined wear threshold, so that the increase in wear on the element is measured continuously between the wear threshold and a maximum wear level.

Advantageously, the electromagnetic radiation transmitted from the external space to the internal space consists of visible light, the tire or tires equipping the same motor vehicle.

Another aim of the present invention is to propose a tire for implementing this wear measurement method, the tire being delimited radially by an internal face and by tread pattern elements intended to be in contact with the ground by means of their respective tops from the very beginning or at a given moment in the running.

According to the invention, the tire comprises in its mass at least one electromagnetic radiation transmission means which is designed to be able to transmit, through at least one of the elements, incident radiation issuing from the space external to the tire to the space internal thereto, as from the time when the transmission means is flush with the surface of the top of the element.

The or each transmission means is preferably permeable to visible light (i.e. being translucent or transparent) and can be formed from one or more mineral or organic materials.

Tests carried out show that the rigidity and the area of the axial section (i.e. in the axial plane of the tire perpendicular to its median circumferential plane) of the transmission means determine the ability of the latter to remain in place during running in the course of the life of the tire. This is because a transmission means will have all the more tendency to be ejected from the tire when any local discontinuities of rigidity with the adjacent compositions of the tire are higher (i.e. this means will be more rigid), for the same area of the axial section characterizing it.

According to a first example embodiment of the invention, the or each transmission means consist of one or more relatively rigid materials each having a modulus of elasticity MA10 (at 10% deformation), measured in accordance with ASTM D 412 of 1998, which is between 1 GPa and 10 GPa (this material advantageously being based on glass, quartz or a plastic comprising a choice of a thermoplastic polymer such as a polystyrene, a methyl polymethacrylate, a polycarbonate, a polyamide, a polyvinyl chloride, a polyester or a thermosetting polymer).

It is possible for example to use one or more optical fibers opening out in the internal space, which are each formed by a core based on glass, silica or quartz and a sheath based on a thermoplastic polymer or a glass, silica or quartz with a refractive index less than that of the core.

It is also possible to use one or more optical fibers which are each formed from plastics such as those mentioned (the sheath of the optical fiber or fibers being formed from a plastic with a refractive index less than that of the core).

It is also possible to use as transmission means one or more assemblies, rectilinear or not, of optical fibers with a very small cross-section (diameter between 50 μm and 100 μm) which are each embedded in a sheath consisting of a rubber composition designed to mechanically decouple each optical fiber assembly from the adjacent rubber compositions in the tire.

Each optical fiber assembly is advantageously of the same type as those used for producing the cables used as metallic or textile reinforcements in tires (i.e. twisted cables or cables with layers with a finite or infinite winding pitch), and each assembly has an increased resistance to breakage caused by the deformations in running on the crown of the tire. It is possible for example to use assemblies or bundles of fibers each comprising from around ten to around a hundred optical fibers.

It should be noted that these optical fiber assemblies are particularly advantageous for implementing the wear measurement method according to the invention, because on the one hand of the excellent light transmission coefficient of this type of material, which makes it possible to use assemblies with a diameter of less than 1 mm, and on the other hand the absence of changes in these assemblies over time and under the thermomechanical stresses caused during the life of the tire.

Preferably, the or each transmission means consisting of this relatively rigid material or materials will have an axial section with a very much reduced area (for example like that of an optical fiber), so as to minimize any discontinuities in rigidity with the adjacent compositions and thus remain durably in place, following prolonged running.

It should be noted that this minimization of the area of the axial section of the or each transmission means can be compensated for by the use of a very high radiation transmission coefficient for this transmission means and/or by providing a plurality of such transmission means in the tire, for a given quantity of energy transmitted.

According to a second preferential example embodiment of the invention, the or each transmission means consists of at least one rubber composition based on at least one elastomer having a modulus of elasticity MA10 (at 10% deformation), measured in accordance with ASTM D 412 of 1998, which is between 1 MPa and 20 MPa (this elastomer advantageously belonging to the family consisting of cross-linkable elastomers, thermoplastic elastomers, true polyurethanes and polyurethane derivatives, such as polyurethane/urea, polyureas, polyurea/urethane, polyurethane/isocyanurate, polyurea/isocyanurate or polyurethane/urea/isocyanurate).

Preferably, use is made of dienic elastomers which can either be vulcanized or cross-linked with peroxides. It is possible to cite for example polybutadienes, polyisoprenes or styrene/butadiene copolymers. It is also possible to use elastomers with a reduced number of double bonds such as EPDMs (ethylene, propylene and diene terpolymers) or butyl rubbers (isoprene and isobutylene copolymers), halogenated or not.

Even more preferentially, use is made of polyisoprenes, styrene/butadiene copolymers, isoprene/styrene copolymers or polybutadienes.

By way of translucent rubber composition which can be used in these transmission means consisting of rubber, use is advantageously made of compositions with no staining element and strong ingredients which are not soluble or dissolve only with difficulty in the translucent composition, which comprise:

paraffin oils by way of plasticizing oil, instead of the usual aromatic or even naphthenic oils, non-staining phenolic antioxidants as an antioxidant, instead of the usual antiozonants which result in significant browning of the composition, a reinforcing inorganic filler such as silica, in reduced quantities, by way of reinforcing filler instead of carbon black (which is excluded in these translucent compositions).

In the present application, "reinforcing inorganic filler", in known manner, is understood to mean an inorganic or mineral filler, whatever its color and its origin (natural or synthetic), also referred to as "white" filler or sometimes "clear" filler in contrast to carbon black, this inorganic filler being capable, on its own, without any other means than an intermediate coupling agent, of reinforcing a rubber composition intended for the manufacture of tires, in other words being capable of replacing a conventional tire-grade carbon black filler in its reinforcement function.

Advantageously, the entirety or at the very least a majority proportion of said reinforcing inorganic filler is silica. The silica used may be any reinforcing silica known to persons skilled in the art, in particular any precipitated or fumed silica having a BET surface area and a CTAB specific surface area both of which are less than 450 m$^2$/g, even if highly dispersible precipitated silicas are preferred. Silica having BET or CTAB specific surfaces in the range of 80 m$^2$/g to 260 m$^2$/g are preferably used.

In the present specification, the BET specific surface area is determined in known manner, in accordance with the method of Brunauer, Emmet and Teller described in "The Journal of the American Chemical Society", vol. 60, page 309, February 1938, and corresponding to AFNOR-NFT-45007 (November 1987); the CTAB specific surface area is the external surface area determined in accordance with the same AFNOR-NFT-45007 of 1987.

"Highly dispersible silica" is understood to mean any silica having a very substantial ability to disagglomerate and to disperse in an elastomeric matrix, which can be observed in known manner by electron or optical microscopy on thin sections. As non-limitative examples of such preferred highly dispersible silicas, mention may be made of the silicas Ultrasil 7000 and Ultrasil 7005 from Degussa, the silicas Zeosil 1165MP, 1135MP and 1115MP from Rhodia, the silica Hi-Sil EZ150G from PPG, the silicas Zeopol 8715, 8745 and 8755 from Huber, and treated precipitated silicas such as, for example, the silicas "doped" with aluminum described in application EP-A-735 088.

The physical state of the reinforcing inorganic filler is immaterial, whether it be in the form of a powder, microbeads, granules or alternatively balls. Of course, "reinforcing inorganic filler" is also understood to mean mixtures of different reinforcing inorganic fillers, in particular of highly dispersible silicas as described above.

As reinforcing inorganic filler, there may also be used for example:

aluminas (of formula $Al_2O_3$), such as the high-dispersibility aluminas which are described in the European patent document EP-A-810 258, or alternatively, aluminum hydroxides, such as those described in the international patent document WO-A-99/28376.

Also suitable are reinforcing inorganic fillers comprising carbon blacks modified by silica such as, for example, the fillers sold by CABOT under the name "CRX 2000", which are described in the international patent document WO-A-96/37547.

The translucent rubber composition according to the invention furthermore comprises, in conventional manner, a reinforcing inorganic filler/elastomeric matrix bonding agent (also referred to as coupling agent), the function of which is to ensure sufficient chemical and/or physical bonding (or coupling) between said inorganic filler and the matrix, while facilitating the dispersion of this inorganic filler within the matrix.

Advantageously, the or each transmission means based on this elastomer or elastomers can have an axial cross-section with a relatively large area, because of the fairly insignificant difference in rigidity compared with the adjacent rubber compositions, and can on the other hand have a relatively small coefficient of transmission for a given quantity of energy transmitted.

According to a preferential embodiment of the invention in accordance with this second example, the tire is such that all the rubber compositions situated radially inside the wear indicator or indicators (i.e. including the or each transmission means) are translucent, comprising neither carbon black nor darkening agent.

According to a third example embodiment of the invention, the or each transmission means can advantageously comprise a core intended to transmit radiation, based on at least one relatively rigid material, as defined above in the first example embodiment, which is enveloped with a compressible deformable sheath designed to mechanically decouple the core from the adjacent rubber compositions in the tire. This sheath is preferably based on a cellular rubber and has a modulus of elasticity MA10, measured in accordance with ASTM D 412 of 1998, of between 0.1 MPa and 1 MPa.

This transmission means comprising the core and the sheath has for example the form of a bar whose side surface (consisting of the sheath) can advantageously be cylindrical, prismatic, conical or pyramidal in shape.

It should be noted that this core can advantageously have both a high coefficient of transmission and an also large axial section area, like the second example embodiment.

The sheath is preferably based on a cellular rubber with closed cells in order to prevent the absorption of water and in particular the diffusion of inflation gas in the structure of the tire (in particular in the plies and cables of the carcass reinforcement).

By way of example, it is possible to use glass for the core and, for the sheath, butyl foam, polychloroprene, a butadiene and acrylonitrile copolymer (NBR), an ethylene, propylene and diene terpolymer (EPDM), or a rubber composition used in the tire which has been expanded.

The tires according to the invention can be manufactured as follows.

According to a first embodiment of the invention, each radiation transmission means is formed in the tire during manufacture, before the curing of the corresponding cover ("cover" means in the present invention the uncured tire, sometimes referred to as the "blank"). It is in this case necessary for the material or materials making up each transmission means to be able to withstand the curing temperature of the tire (typically around 170° C.) without damage.

According to a second preferred embodiment of the invention, each transmission means is formed in the tire after the operation of curing the corresponding cover, preferably by the insertion and possibly adhesive bonding of the or each transmission means in a recess formed in the cured tire.

In accordance with this last preferred embodiment, the or each transmission means has substantially the shape of a drawing pin comprising a head provided with a stem at its center, the stem being contained in a radial recess formed from the internal face to the top of the corresponding tread pattern element, so that the head is in contact with the internal face and the free end of the stem is practically flush with the surface of the top, the head and part of the stem extending from the head being formed from the translucent rubber composition whilst the other part of the stem contained in the free end is formed from at least one opaque rubber composition, the interface radial height between the translucent composition and the opaque composition being designed to correspond to a wear threshold to be detected in the tread pattern element.

According to one advantageous embodiment of the invention, the tire comprises several radiation transmission means which have respectively different colors in the spectrum of the visible range.

Advantageously, the or each transmission means has a cross-section in the axial direction of the tire whose area increases continuously over a given wear height radially towards the inside of the tire, so that the quantity of energy of the radiation transmitted in the internal space increases continuously with the area of the section flush with the surface of the top of the element, when the latter wears.

According to one advantageous embodiment of the invention, the or each transmission means extends over the entire circumference of the tire.

Advantageously, the tire can comprise a plurality of transmission means whose respective heights, in the radial direction of the tire, correspond to various predetermined wear thresholds to be detected for the element.

In the aforementioned case in which the or each radiation transmission means comprises an optical fiber opening out in the internal space, the tire can be provided with at least one wear detection unit which contains:

in a radially uppermost upstream part passing through the internal face and ending in one of the tread pattern elements recessed from its top, the transmission means, which comprise one or more optical fibers parallel to each other which are each designed so as to be able to transmit incident radiation issuing from the space external to the tire to the space internal thereto and whose radial height or heights correspond respectively to one or various predetermined wear thresholds to be detected for the element, and in a radially lower downstream part mounted in the space internal to the tire, a detection means connected to the optical fiber or fibers which is designed to detect the energy of the radiation transmitted to it by the fiber or fibers, from the time when at least one of the fibers is flush with the surface of the top of the tread pattern element.

According to another characteristic of the invention, the wear detection unit comprises, in the downstream part, a transmitter coupled to an antenna for transmitting electrical signals representing measurements of radiated energy and a microprocessor for processing the radiated energy measurements.

Another aim of the present invention is to propose a wheel comprising a rim intended to receive a tire as defined previously, for implementing the also aforementioned wear measurement method.

According to the invention, the wheel rim is provided with a means of detecting the energy of the radiation transmitted by the or each transmission means in the space internal to the tire, as from the time when the or each transmission means are flush with the surface of the top of the tread pattern element because of wear on the latter.

Advantageously, the wheel rim is also provided with a means of quantifying the energy of the radiation transmitted in the space internal to the tire and/or means of locating in the tire each radiation transmission means.

Also advantageously, the wheel rim is also provided with a means of discriminating the colors of the visible radiation transmitted.

According to a preferential embodiment of the invention, the detection means is contained in a wheel module which is mounted on the wheel rim and which is intended to monitor the operating parameters of the tire/wheel assembly, such as its internal pressure and temperature, the wheel module also comprising a transmitter coupled to an antenna for transmitting electrical signals representing measurements of radiated energy, temperature and pressure, and a microprocessor intended to process all the measurements of radiated energy, temperature and pressure.

According to one advantageous example embodiment of the invention, the wheel rim is also provided with means for picking up the radiation received at the surface of the rim in radial directions with respect to the rim surface, and for concentrating this radiation picked up by directing it practically along the rim surface to the radiation detector.

To this end, the rim is for example provided at its bottom with a collar for holding the wheel module, the radially uppermost face of the collar comprising the means for picking up and concentrating the radiation.

Another aim of the present invention is to propose a tire/wheel assembly for implementing the aforementioned wear measurement method, comprising a wheel and a tire mounted on the wheel.

According to the invention, the tire/wheel assembly is such that the tire and the wheel are as defined previously.

Another aim of the invention is to propose a motor vehicle which comprises at least one tire/wheel assembly according to the invention, this vehicle being provided with a receiver intended to receive the signals from the transmitter, a computer connected to the receiver which is intended to process these signals and a display installed in the vehicle cabin which is connected to the computer and which is intended to inform the vehicle driver of the state of wear of the tread pattern elements on the tire or tires.

BRIEF DESCRIPTION OF THE DRAWINGS

The aforementioned characteristics of the present invention, as well as others, will be understood better from a reading of the following description of example embodiments of the invention, given by way of illustration and non-limitingly, the description being made in relation to the accompanying drawings, in which:

FIG. 3 is a schematic view in meridian section of a tire/wheel assembly according to a third embodiment of the invention;

FIG. 4 is an enlargement showing an exploded view of the wear measurement means with which the tire according to the invention in FIG. 3 is provided;

DETAILED DESCRIPTION

Figure 1:
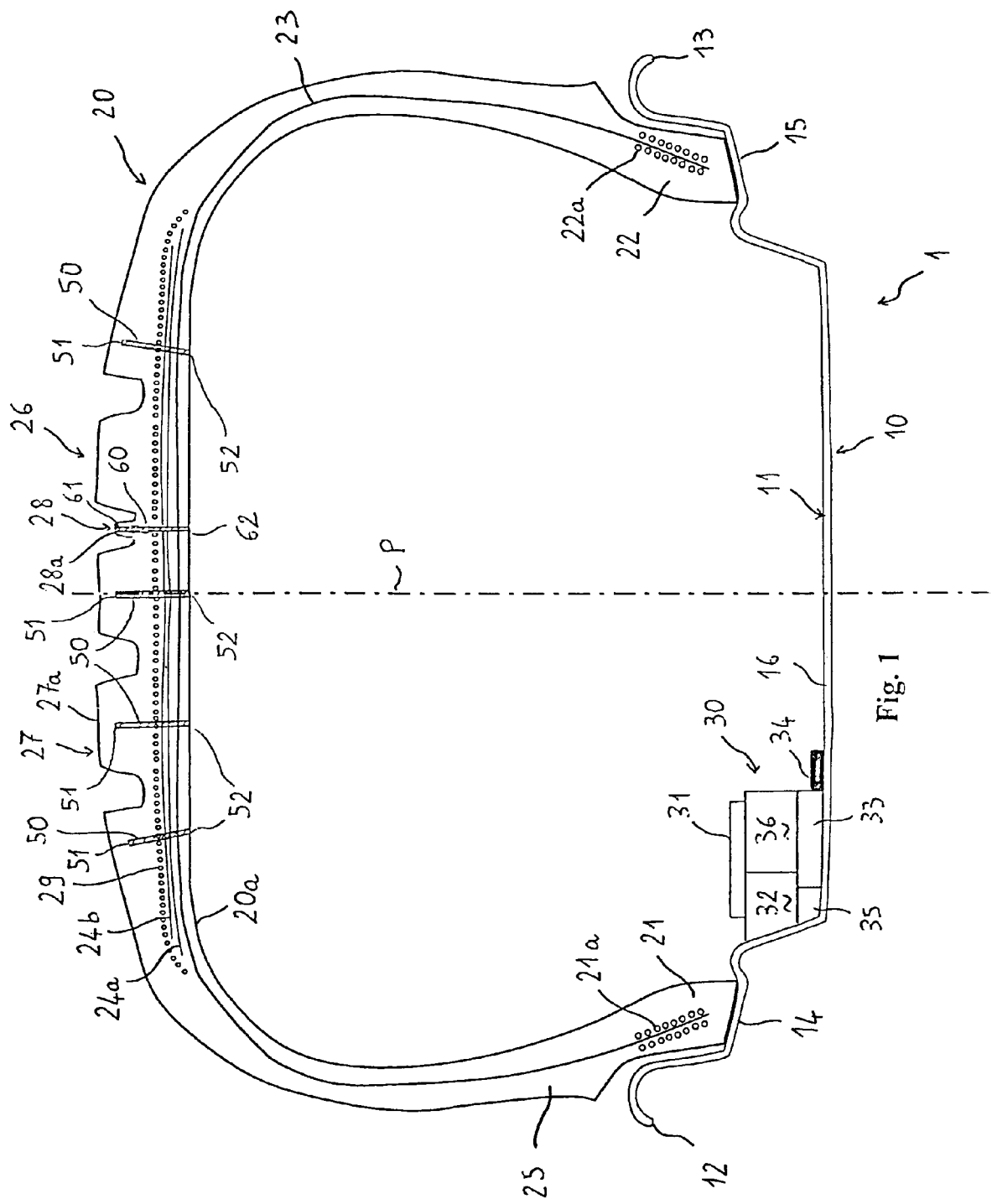
FIG. 1 is a schematic view in meridian section of a tire/wheel assembly according to a first embodiment of the invention.

The tire/wheel assembly 1 depicted in FIG. 1 comprises a wheel 10, a tire 20 which is mounted on the wheel 10 and a wheel module 30 which is also mounted on the wheel 10 between the wheel and the tire 20 and which is in particular intended to monitor operating parameters of the tire/wheel assembly 1, such as its internal pressure and temperature.

For reasons of clarity, only the rim 11 of wheel 10 is illustrated in FIG. 1. This rim 11 comprises, as from its peripheral projections 12 and 13, two rim seats 14 and 15 intended to receive respectively beads 21 and 22 of the tire 20, and a surface 16 which connects these seats together.

It should be noted that the rim 11 of a tire/wheel assembly according to the invention could have any form known in the prior art, in particular comprising seats 14 and 15 more or less inclined towards the inside or towards the outside of the rim 11 and a surface 16 having a non-linear geometry in meridian section, for example comprising one or more grooves or channels.

In the usual fashion, the tire 20 comprises essentially a carcass reinforcement (shown by a carcass ply 23 in FIG. 1) which is radially surmounted by a crown reinforcement (shown by working crown plies 24a and 24b in FIG. 1). The carcass reinforcement 23 is extended laterally from the crown by side walls 25, which terminate in beads 21 and 22 reinforced by bead wires 21a and 22a. A tread 26 comprising tread pattern elements 27, 28 radially surmounts the crown reinforcement.

The tire 20 can also comprise a so-called wrapping ply 29 which for example radially surmounts the crown reinforcement, so as to cover the working crown plies 24a, 24b, and which is in particular characterized in that the cables which reinforce it are disposed in a spiral at an angle of 0° or close to 0° to the circumferential mid-plane P of the tire (it is also known how to dispose relatively narrow strips or plies at an angle of approximately 0° in place of the aforementioned cables, to fulfill a function of wrapping of the crown reinforcement).

It should be noted that the tire 20 of the tire/wheel assembly 1 according to the invention could have a different architecture from that mentioned above, though it must necessarily comprise a tread 26 surmounting carcass and crown reinforcements which comprise composite plies 23, 24a, 24b reinforced by cables.

By way of tread pattern elements 27, 28, FIG. 1 depicts on the one hand first tread pattern elements 27 consisting for example of blocks or circumferential ribs which are intended, when the motor vehicle 40 (depicted symbolically in FIG. 6) comprising the tire/wheel assembly 1 is running, to change by means of their respective tops 27a in contact with the ground as soon as running begins, and on the other hand a second tread pattern element 28 consisting of a "wear indicator" which may have a form similar to that of the first tread pattern elements 27 but having a height substantially less than these elements 27.

In the example in FIG. 1, the tire 20 is provided with a plurality of transmission means 50, 60 which are each designed to be able to transmit incident electromagnetic radiation external to the tire 22, such as visible light, from a radially uppermost upstream end 51, 61 to a radially lower downstream end 52, 62 of these transmission means 50, 60.

There can be seen firstly in FIG. 1 the transmission means 50 which are each disposed in the tire 20, so that their end 51 opens out in a first tread pattern element 27 on the tread 26 whilst facing the top 27a thereof, at a given distance from this top 27a corresponding to a predetermined wear height of this tread pattern element 27, and so that their end 52 opens out on the radially internal face 20a (represented by the internal rubber compound) of the tire 20 and thus communicates with the internal space thereof (i.e. the space included between the tire 20 and the rim 10).

There can also be seen in FIG. 1 the transmission means 60 which is disposed in the tire 20, so that its radially uppermost end 61 opens out in a second tread pattern element 28 or "wear indicator" on the tread 26 whilst being situated radially just below the top 28a thereof, and so that its radially lower end 62 opens out on the radially internal face 20a of the tire 20 and thus communicates with the internal space thereof.

Each radiation transmission means 50, 60 passes through firstly part of the tread 26 and secondly the wrapping ply 29, the working crown plies 24a and 24b and the carcass ply 23.

It should be noted that each transmission means 50 or 60 can consist of any means transparent to one or more electromagnetic radiations (i.e. which allows such radiation to pass) and, preferentially, a means which allows at least visible light to pass.

In the embodiment in FIG. 1, the radiation transmission means 50, 60 each have a cylinder shape whose diameter is for example around 0.5 mm, and are respectively disposed opposite the tops 27a, 28a of the tread pattern elements 27, 28 occupying different positions in the axial direction of the tire 20. One of the transmission means 50 occupies for example a location centered on the circumferential mid-plane P of the tire 20, whilst others occupy axially adjacent positions on each side of this plane P (including the "wear indicator" 28), which may go as far as the shoulder 26a of the tire 20.

The wheel module 30 is provided according to the invention with detection means 31 designed to detect at one or more points in the internal space of the tire 20 the energy of light radiation transmitted by each transmission means 50 or 60. The detection means 31 can consist of an electrically passive detector, such as a photovoltaic cell, or an electrically active detector such as a photoelectric detector advantageously consisting of a photodiode (a semiconductor diode producing an electric current by absorption of the light radiation).

Optionally, the radiation detection means 31 is coupled to a means of quantifying the transmitted radiation (not shown) which is designed to quantify the energy of the radiation transmitted in the space internal to the tire 20.

It should be noted that the transmission means 50, 60 can be formed respectively from materials of different colors in the visible range spectrum, for example based on translucent and colored rubber compositions, for modulating the quantities of light energy transmitted by these means 50, 60 inside the tire 20 (for example blue light conveys approximately twice as much energy as red light).

It should also be noted that different radial heights for the radially uppermost ends 51, 61 of the transmission means 50, 60 (corresponding to more or less critical wear heights of the tread pattern elements 27, 28) can be respectively associated with different colors for the means 50, 60.

Also optionally, the wheel module 30 can be provided with means for locating in the tire 20 each radiation transmission means 50, 60, and/or means of discriminating the colors of the transmitted radiation (these location and discrimination means are not shown).

The locating means can for example consist of n-1 separating flaps which are impermeable to the transmitted radiation in question and whose function is to practically divide the internal space of the tire 20 into n zones respectively situated opposite the n transmission means 50, 60. It is also possible to use locating means consisting of lenses, reflective surfaces of the mirror type, or a combination of several of these elements, including separating flaps.

The means of discriminating the colors of the transmitted radiation can for example consist of a filter or a prism.

Still optionally, the wheel module 30 can be provided, upstream of the detection means 31 and/or means of quantifying the transmitted radiation, with means, such as a lens, for focusing the radiation transmitted by each or all of the transmission means 50, 60 (i.e. for concentrating it at a focus), or on the other hand for diffracting this transmitted radiation.

The wheel module 30 in particular also comprises:

sensors 32 intended to measure the pressure and temperature in the space internal to the tire 20, a high-frequency radio transmitter 33 coupled to an antenna 34 for transmitting, in the direction of a radio receiver 41 which is mounted on the vehicle 40 (see FIG. 6) outside the tire/wheel assembly 1, electrical signals representing measurements of radiated energy, temperature and pressure, a battery 35 for the electrical supply to the wheel module 30, and a microprocessor 36 intended to provide the preparation and a first processing of all the measurements of radiated energy, temperature and pressure, as well as management of the frequency of communications with the vehicle 40 (battery economizer function 35) and intended to provide control of the radio transmissions (it should be noted that this microprocessor 36 could integrate the aforementioned sensors 32).

Figure 2:
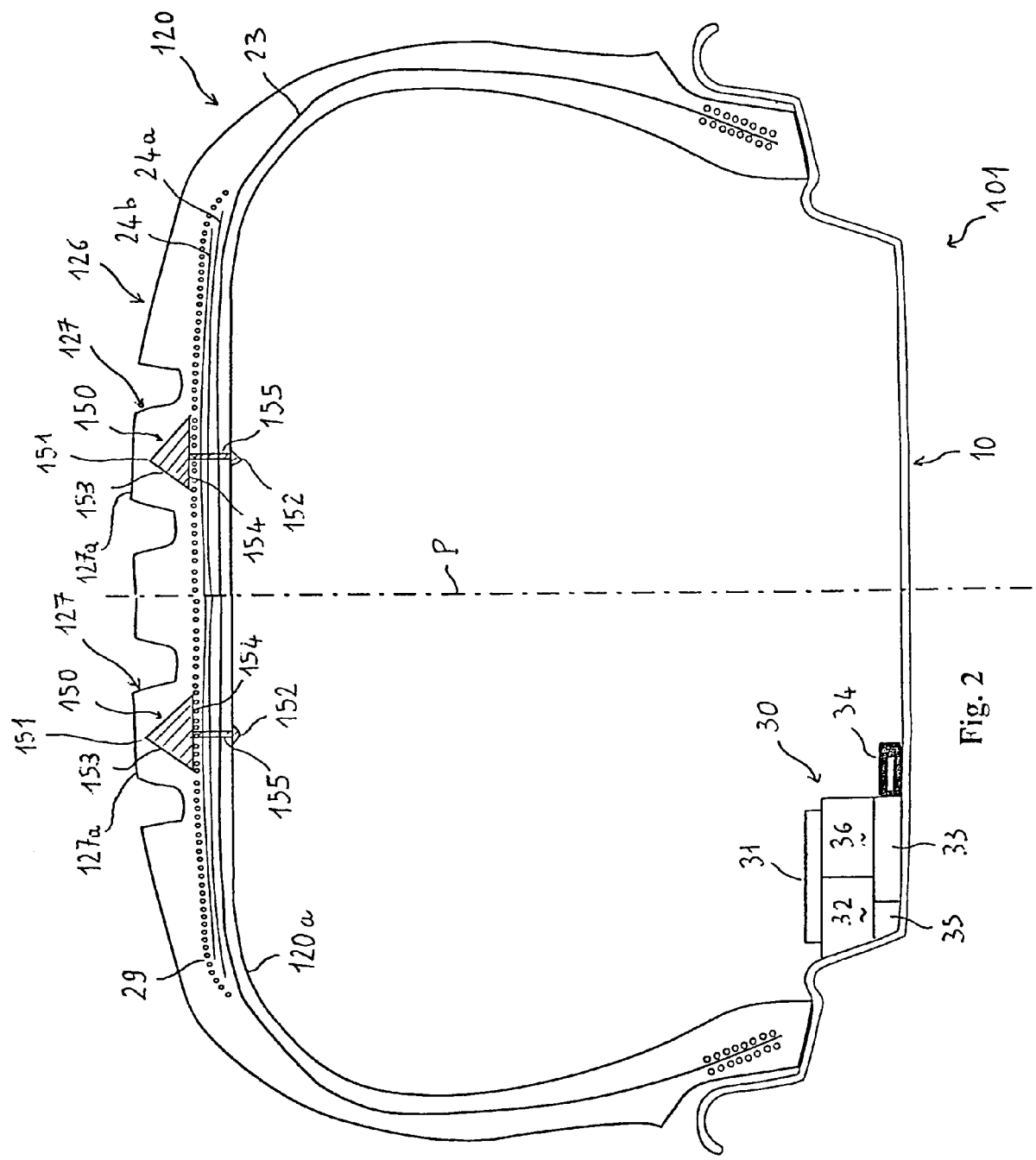
FIG. 2 is a schematic view in meridian section of a tire/wheel assembly according to a second embodiment of the invention.

For the description of the following figures, the numerical references in FIG. 1 have been kept for elements having identical structural characteristics and have been increased by 100 as from FIG. 2 for elements or means having identical functional, if not structural, characteristics.

The tire/wheel assembly 101 of FIG. 2 is differentiated from that of FIG. 1 solely in that each radiation transmission means 150 with which it is provided is formed from a material transparent at least to visible radiation (preferably a translucent rubber composition) and in that it has a given geometry formed by two distinct parts (153 and 155) which can be formed from identical or different materials.

Each radiation transmission means 150 is delimited radially by a radially upper upstream end 151 opening out in a tread pattern element 127 on the tread 126 whilst facing the top 127*a* thereof, at a given distance from this top 127*a* corresponding to a predetermined wear height of this tread pattern element 127, and by a radially lower downstream end 152 opening out on the radially internal face 120*a* of the tire 120 and thus communicating with the internal space of the latter.

More precisely, each transmission means 150 comprises an upstream part 153 which is delimited radially by the radially uppermost end 151 and by a radially lower base 154 surmounting the wrapping crown ply 29 which is radially uppermost, so that the cross-section of the upstream part 153 increases radially from the end 151 to the base 154.

In the example in FIG. 2, this upstream part 153 has a conical shape. It should be noted that it could also have a pyramidal or prismatic shape or a frustoconical or truncated pyramid shape, provided that its section increases in the radially lower direction of the tire 120.

Each transmission means 150 also comprises a downstream part 155 which extends radially from the base 154 to the radially lower end 152, and which passes through the cap ply 29, the working crown plies 24*a* and 24*b* and the carcass ply 23 of the tire 120. As can be seen in FIG. 2, this downstream part has a constant cross-section in the radial direction of the tire 120 and has for example a cylinder shape whose diameter is similar to that of each transmission means 50, 60 in FIG. 1.

The tire/wheel assembly 101 in this FIG. 2 comprises a wheel module 30 having all the characteristics mentioned above in relation to FIG. 1, this module 30 being in particular provided with the detection means 31 designed to detect the energy of transmitted radiation and possibly the quantification means designed to quantify the energy of this transmitted radiation, the means of locating each transmission means 150, the means of discriminating the colors of the transmitted radiation and the focusing or diffraction means.

Figure 5:
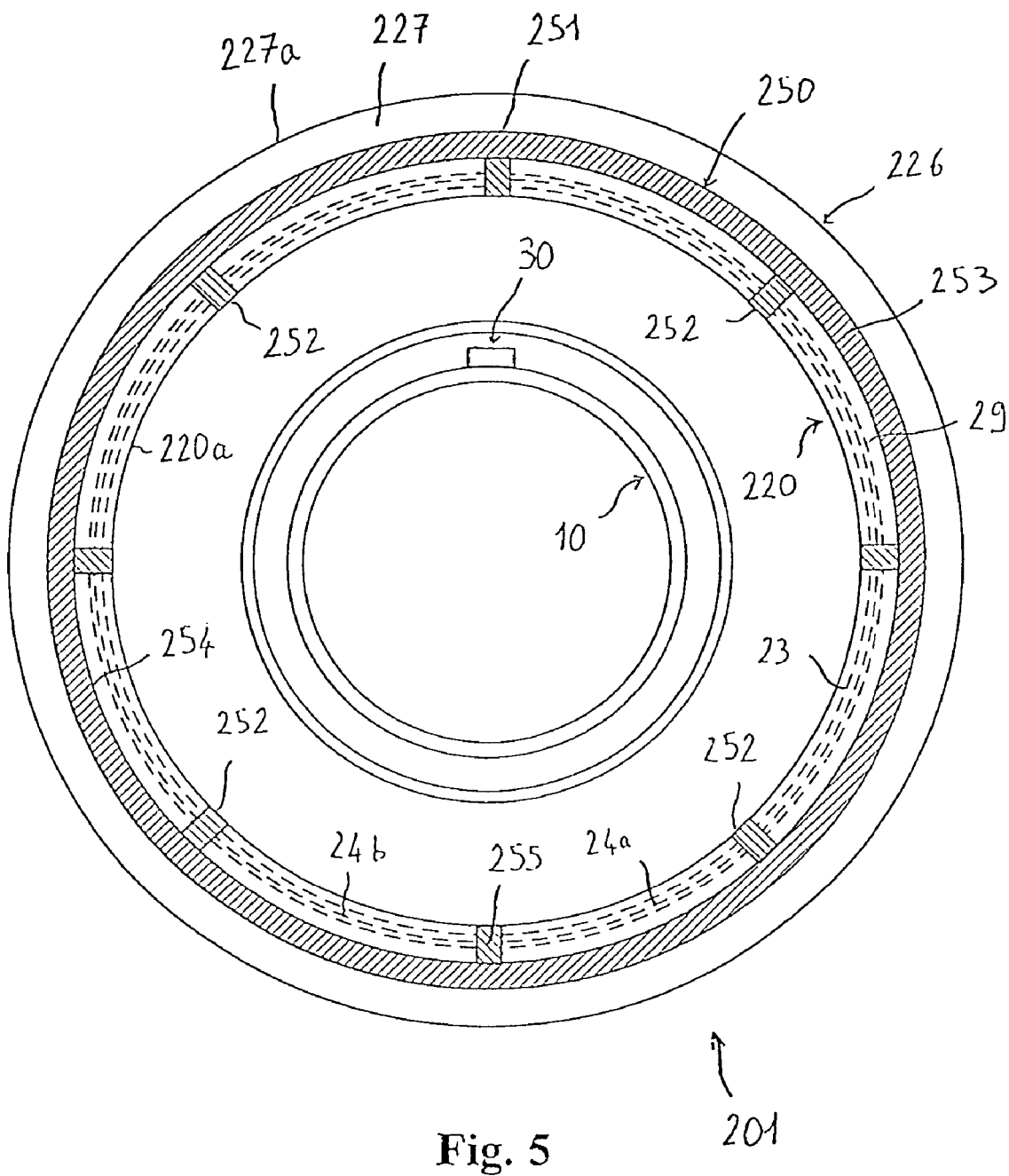
FIG. 5 is a schematic view in section along the circumferential mid-plane V—V of FIG. 1 of a variant embodiment of the tire/wheel assembly of FIG. 2.

The tire/wheel assembly 201 depicted in FIG. 5 shows a variant of the embodiment illustrated in FIG. 2. This tire/wheel assembly 201 is differentiated from those in FIGS. 1 and 2 solely by the geometry of transmission means 250 with which the tire 220 is provided in its mass.

Transmission means 250 extends over the entire circumference of the tire 220 and is delimited radially by a radially uppermost upstream perimeter 251 opening out in a tread pattern element 227 of the tread 226 whilst facing the top 227*a* of the latter, at a given distance from this top 227*a* corresponding to a predetermined wear height of this tread pattern element 227, and by a plurality of radially lower downstream ends 252 opening out on the radially internal face 220*a* of the tire 220 and thus communicating with the space internal to the latter.

More precisely, transmission means 250 comprises an upstream part in the form of a ring 253 with a reduced thickness in the axial direction of the tire 220 (i.e. a practically flat ring in the form of a circumferential groove), which is delimited radially by the radially uppermost perimeter 251 and by a radially lower perimeter 254 surmounting the cap ply 29 which is radially uppermost, so that the cross-section of the upstream part 253 is constant in the radial direction of the tire 220.

It should be noted that this upstream part 253 could have a more significant axial thickness, for example an elliptic (in particular circular) or polygonal (in particular rectangular) shape in the axial direction of the tire 220, conferring on it for example a substantially torus or annular volume shape. In this case, the upstream part 253 could be delimited by radially upper and lower surfaces 251 and 254, instead of the aforementioned perimeters.

Transmission means 250 also comprises a plurality of downstream parts 255 regularly spaced apart over the circumference of the tire 220, which each extend radially from the radially lower perimeter or surface 254 to one of the corresponding radially lower ends 252, and which pass through the cap ply 29, the working crown plies 24*a* and 24*b* and the carcass ply 23 of the tire 220. Like the downstream part 155 in FIG. 2, this downstream part 255 has for example a constant cross-section in the radial direction of the tire 220 and has for example a cylinder shape whose diameter is similar to that of the downstream part 155.

It should be noted that the tire 220 in FIG. 5 can be provided with several radiation transmission means 250 distributed over the width (axial dimension) of the tire 220.

The tire/wheel assembly 201 in this FIG. 5 comprises a wheel module 30 also having all the characteristics mentioned above in relation to FIG. 1.

The tire/wheel assembly 301 in FIG. 3 is differentiated essentially from the one in FIGS. 1, 2 or 5 in that the tire 320 which it has is provided in its mass with at least one wear detection unit 370 which incorporates:

in a radially uppermost upstream part 371, radiation transmission means 350 comprising optical fibers 372 to 377 (see the insert in FIG. 4), and in a radially lower downstream part 378, a detection means or photodetector 331 (electrically active or passive, used in this case in photovoltaic mode) fixed to these optical fibers 372 to 377, which is provided for detecting the radiation energy specifically transmitted by each fiber 372 to 377, and an electronic unit 333 comprising a radio transmitter coupled to an antenna for transmitting electrical signals representing the measurements of radiated energy in the direction of the radio receiver 41 mounted on the vehicle 40 (FIG. 6), and a microprocessor for processing the measurements of radiated energy, as well as management of the frequency of the communications with the vehicle 40.

FIG. 3 depicts a tread pattern element 327 consisting of a parallelepipedal-shaped "block" or a rib which is provided in its mass with the detection unit 370, which extends radially through the tire 320 from the radially internal face 320*a* thereof and as far as the inside of the element 327.

As can be seen in FIG. 3, the unit 370 has substantially the shape of a drawing pin (i.e. a head forming the downstream part 378 on which there is mounted a point forming the upstream part 371).

Inside the unit 370, the optical fibers 372 to 377 and the detection means 331 are covered with a coating composition 379 which is identical to that of the tread 326 or compatible therewith.

As can be seen in FIG. 4, the optical fibers 372 to 377 are mounted in a specific manner on the photodetector 331, which comprises locations 331*a* respectively intended to receive them.

The photodetector 331 has a circular shape and at its center there is mounted a reference optical fiber 372 of maximum height amongst the set of fibers 372 to 377 (this maximum height corresponding to a predetermined wear threshold of the tread pattern element 327). Around this reference fiber 372 there are mounted in a circle and at equal distances from each other the optical fibers 373 to 377 (measurement optical fibers) comprising a fiber 373 with a height equal to that of the reference fiber 372 followed by the fibers 374 to 377 whose height decreases in a regular fashion over the circumference of the photodetector 331, so that the fiber 377 of minimum height is adjacent to the fiber 373 of maximum height.

The locations 331*a* of the photodetector 331 are connected by cables 331*b* to the electronic unit 333 for the processing of the signals generated by this photodetector 331.

It should be noted that these various heights of the measurement optical fibers 373 to 377 correspond respectively to wear thresholds to be detected for the tread pattern element 327 and that the wear measurements could be refined further by providing an increased number of measurement optical fibers where the differences in height are lesser over the circumference of the photodetector 331.

As can be seen in FIG. 3, the downstream part 378 of the unit 370 is mounted in contact with the radially internal face 320*a* of the tire 320 by means of a shoulder which its internal fixing face forms with the upstream part 371.

It should be noted that the downstream part 378 can have any suitable geometry (circular or rectangular cross-section etc), provided that it matches the shape of this internal face 320*a* at the location provided for its fixing. This downstream part 378 can advantageously have a broadening of its cross-section in the direction of its internal fixing face (a frustoconical or prismatic shape for example).

As for the upstream part 371 of the detection unit 370, this can also have various geometries, for example parallelepipedal or cylindrical shapes.

The unit 370 was incorporated in the tire 320 when the latter was manufactured, by fixing the shoulder of the downstream part 378 and the upstream part 371 to a location of the tire 320 which is provided for this purpose. This location has for example the shape of a cavity with a rectangular cross-section which is intended to receive the upstream part 371.

This incorporation of the unit 370 in the tire 320 is preferably carried out after the curing of the latter, by insertion and adhesive bonding of the unit 370 in a recess formed in the cured tire 320.

Figure 6:
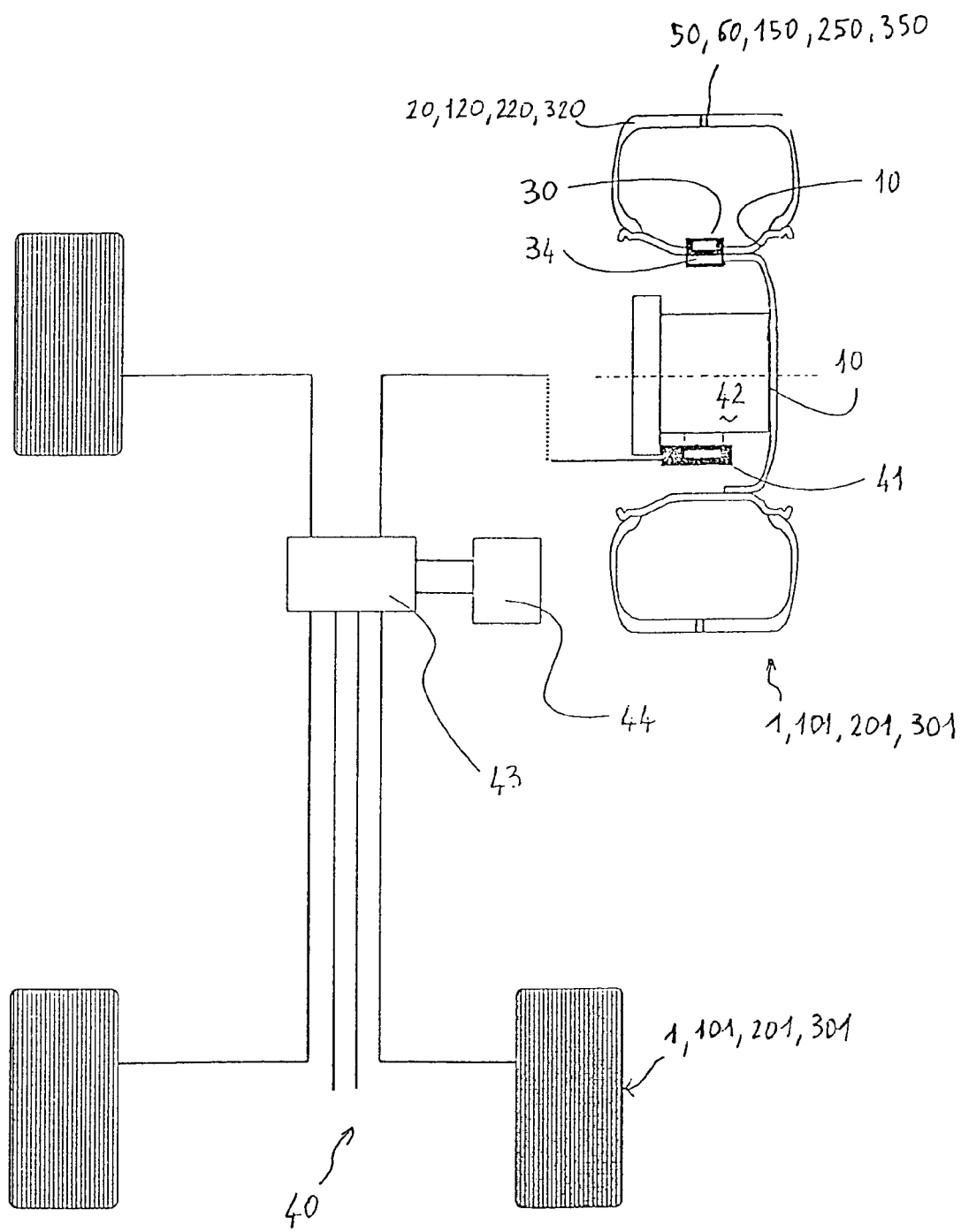
FIG. 6 illustrates schematically and partially the mounting of a tire/wheel assembly according to the invention on the chassis of a motor vehicle according to the invention, as well as the transmission of information from the tire/wheel assembly to the interior of the vehicle.

FIG. 6 depicts schematically the motor vehicle 40 equipped with mounted assemblies 1, 101, 201, 301, at least one of which (depicted in cross-section as well as the wheel stub axle 42 on which it is mounted) is in accordance with the present invention (for example as described with reference to one of FIGS. 1 to 5).

There are shown on this tire/wheel assembly 1, 101, 201, 301, on the one hand the means 50, 60, 150, 250, 350 of transmitting radiation from the external space (ambient air) to the internal space of the tire/wheel assembly 1, 101, 201, 301 (including inside the detection box 370, in the case of the transmission means 350 of FIG. 3). In addition, the tire/wheel assembly 1, 101, 201, 301 includes the wheel module 30 incorporating the pressure and temperature sensors, the radio transmitter coupled to an antenna 34 for transmitting electrical signals representing measurements of radiated energy, pressure and temperature in the direction of the radio receiver 41 mounted on the vehicle 40, and the microprocessor for processing the radiated energy measurements, as well as management of the frequency of the communications with the radio receiver 41 (the sensors, the radio transmitter and the microprocessor not being shown for reasons of clarity).

FIG. 6 shows a computer 43 with which the vehicle 40 is provided, which integrates the operating laws of the tire 20, 120, 220, 320, this computer 43 being connected to the radio receiver 41 and being intended to manage the display of the results of measurements made, from the use which is made thereof upstream.

There is also depicted a display 44 which is connected to the computer 43 and which is for example installed on the dashboard of the vehicle 41, this display being for example intended to continuously inform the driver of the vehicle 40 of the state of wear of the tread pattern elements 27, 28, 127, 227, 327 of the tire or tires 20 to 320.

Figure 7:
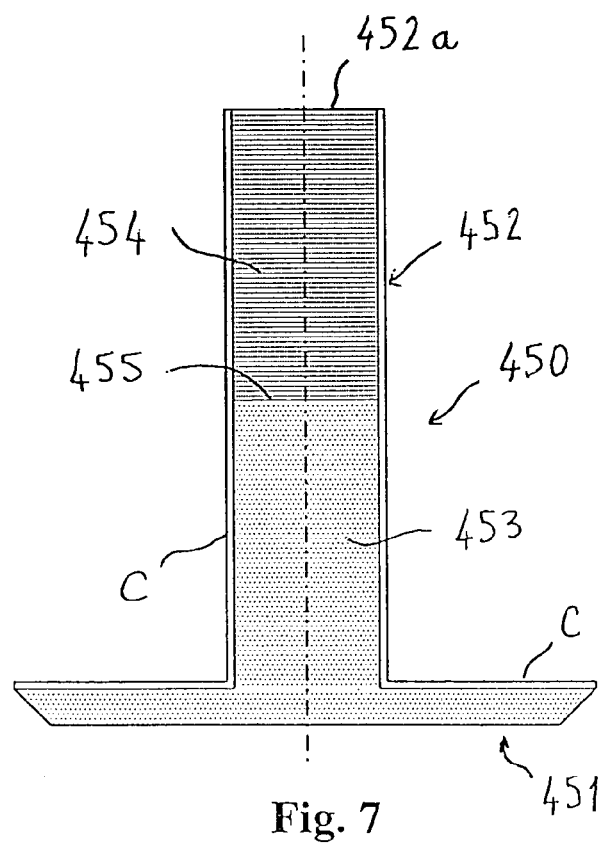
FIG. 7 is a view in axial section of a radiation transmission means according to an example embodiment of the invention for measuring wear.

FIG. 7 is a view in axial section of a radiation transmission means 450 according to one example embodiment of the invention. This transmission means 450 having in the example in FIG. 7 a symmetry of revolution, the cutting plane considered here contains the axis of symmetry of the means 450.

This transmission means 450 has substantially the shape of a thumb tack, comprising a head 51 practically in the form of a thin disc which is provided with a cylindrical stem 452 at its center. The means 450 is intended to be introduced through the radially internal face 420*a* of the tire 420 (i.e. the internal layer) after the curing thereof, in a radial cylindrical recess 480 previously formed in the outer casing before it is cured or during its curing (this radial recess 480, formed from the internal face 420*a* to the external face of the casing 427*a*, is visible in FIG. 9, so that the head 451 of the means 450 is in close contact with the internal face 420*a* and the free end 452*a* of the stem 452 is practically flush with the radially external surface 427*a* of the tread pattern element 427 whose wear is to be measured (see FIG. 9).

Figure 9:
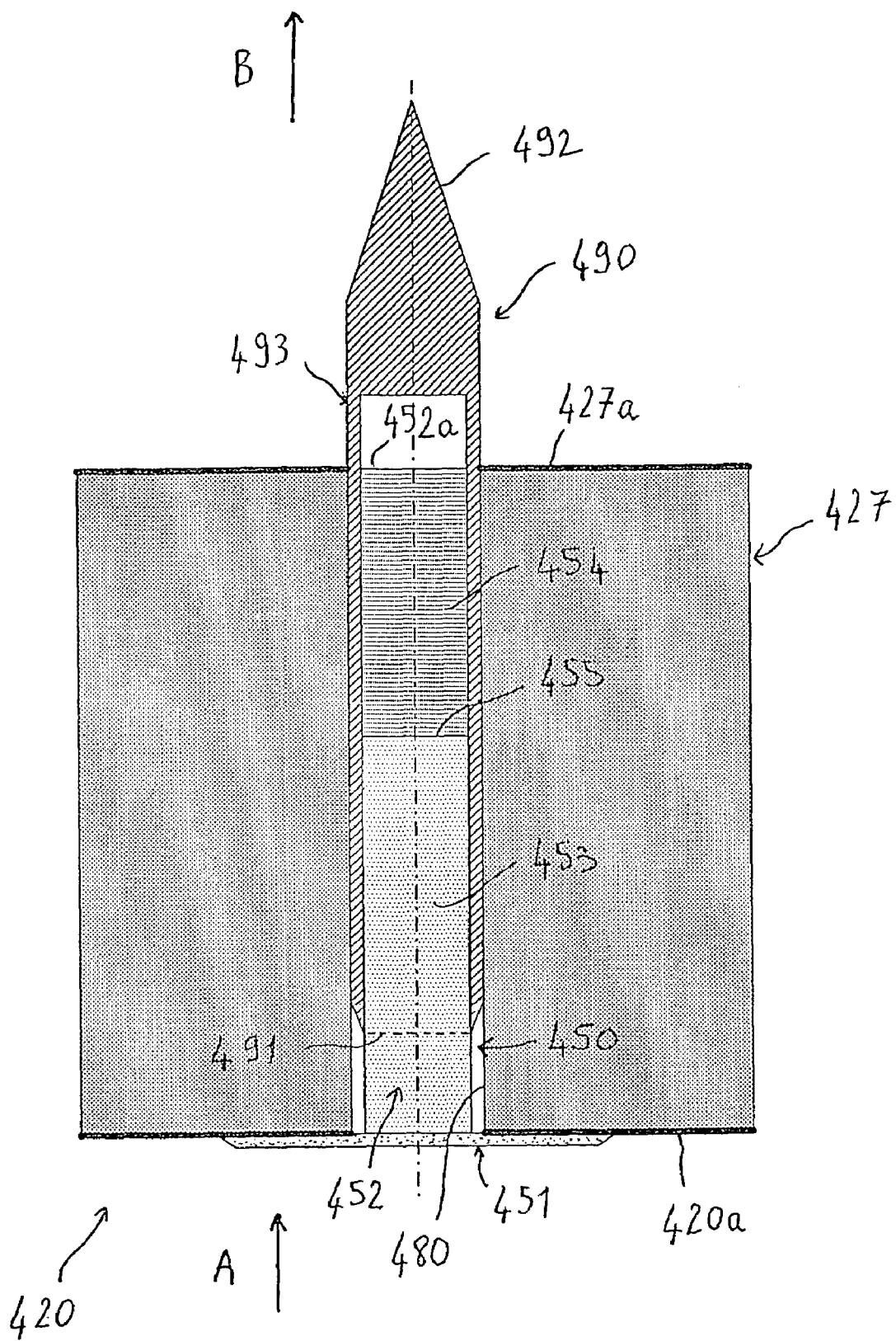
FIG. 9 is a schematic view in meridian section of a tire showing the transmission means of FIG. 7 having been introduced into the mass of the tire by the introduction means of FIG. 8.

As can be seen in FIG. 7, the means 450 is formed by a translucent rubber composition part 453 and an opaque rubber composition part 454 which are respectively situated to form a border at a predetermined interface height 455 of the stem 452, which height is designed to correspond to a wear threshold to be detected in the tread pattern element 427 of the tire 420 (see FIG. 9).

In the example in FIG. 7, the head 451 and the translucent rubber composition part 453 of the stem 452 extending from the head 451 containing are formed from the same translucent composition, which is obtained by molding or injection, whilst the opaque rubber composition part 454 of the stem 452, ending in the free end 452a, is formed from the opaque composition, which may be chosen, for example, to be identical to the rubber composition used for the tread.

The translucent composition 453 comprises an elastomer matrix consisting for example of a polyisoprene, a styrene/butadiene copolymer, an isoprene/styrene copolymer or a polybutadiene, and also comprises:

- a paraffin oil instead of the aromatic or naphthenic oils,
- non-staining phenolic antioxidants instead of the antiozonants which result in significant browning of the composition,
- silica by way of reinforcing filler instead of carbon black.

It will be understood that the interface 455 between these two compositions 453 and 454 can be provided closer to the head 451 or the free end 452a, according to the selected wear threshold.

Two methods, which may be used separately or in combination, of introducing and holding the transmission means 450 in the recess 480 in the tire 420 are described.

A first method consists of mechanically clamping the stem 452 by the rubber wall of the recess 480, obtained by the choice of a diameter of the stem 452 which is greater than that of the recess 480 and by housing this stem 452 inside an insertion means 490 consisting of a metallic sheath in the form of a needle (shown in axial section in FIG. 8) intended to allow the insertion of the stem 452 in the tire 420, so that the head 451 and the free end 452a are disposed in the aforementioned manner.

Figure 8:
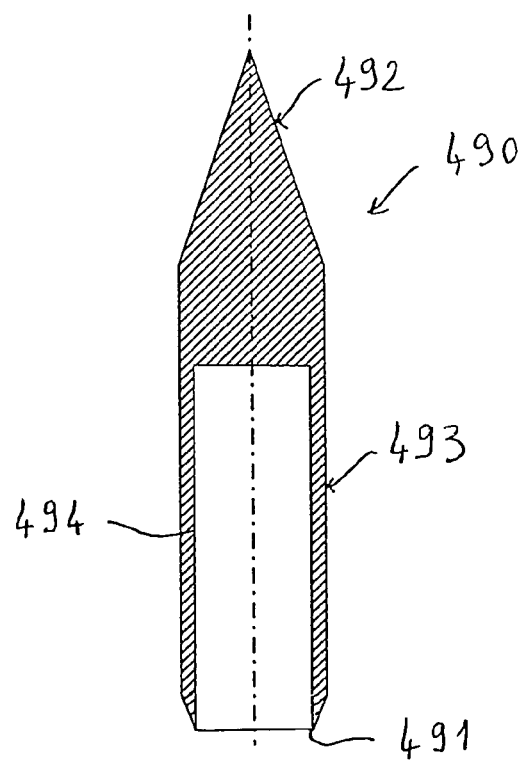
FIG. 8 is a schematic view in axial section, according to an example embodiment of the invention, of an introduction means which can be used for introducing into the tire a transmission means according to the invention such as the one in FIG. 7, through the radially internal face of the tire.

As can be seen in FIG. 8, the sheath 490 comprises, at one of its ends, an opening 491 to allow the axial insertion of the stem 452, and at its other end, a frustoconical tip 492 intended to facilitate the insertion of the sheath 490 in the recess 480 of smaller diameter. The sheath 490 comprises, between the opening 491 and the tip 492, a cylindrical portion 493 hollow over at least part of its length, which forms a tubular housing intended to contain at least part of the stem extending from its free end 452a (the length of the housing being less than that of the stem 452).

By way of example, the inventors have made use of transmission means 450 in which the diameter of the head 451 is 20 mm and the diameter of the stem 452 between 1 mm and 5 mm. A coefficient of clamping of the stem 452 by the recess 480 ranging from 0% to 30% has been used (this coefficient of clamping being defined as being the ratio of the difference between the diameters of the recess 480 and of the stem 452 to the diameter of the recess 480). The diameter of the recess 480 for this transmission means can vary from 1 mm to 4 mm.

Use has also been made of sheaths 490 with a total length L ranging from 40 to 60 mm and whose hollow cylindrical portion 493 is delimited by an annular wall 494 with a thickness of 0.3 mm. As for the inside diameter of this wall 494, this is slightly greater than the diameter of the stem 452 which it is intended to contain.

FIG. 9 illustrates the insertion of the sheath 490 in the recess 480, through the internal face 420a of the tire 420 (for reasons of clarity, the various cable plies are not shown). It can be seen that the head 451 of the means 450 remains outside the opening 491 of the sheath 490 when the stem 452 is housed in the latter.

In a first step of this insertion (see arrow A), the sheath 490 is pressed into the recess 480, which has the effect of expanding the latter by increasing its diameter, until the tip 492 and an adjacent part of the cylindrical portion 493 project radially outside the external face 427a.

In a second step (illustrated by the arrow B), a traction is exerted, for example via a clamp (not shown), on the part 493 of the sheath 490 projecting outside the tire 420, which allows the radial passage of the stem 452 in the recess 480 because of the elasticity of the adjacent rubber compositions and brings the head 451 of the means 450 precisely under the internal face 420a.

In a third step consisting of the complete extraction of the sheath 490 radially outside the tire 420 because of the aforementioned traction, the recess 480 regains its initial diameter and its wall clamps the stem 452 radially, which keeps the means 450 securely in this position during the subsequent running of the tire 420.

A second method of inserting and holding the transmission means 450 of FIG. 7 in the recess 480 in the tire 420 depicted in FIG. 9 consists of fixing this means 450 to the wall of the recess 480 by means of an adhesive of the dual component type, without necessarily having to carry out a mechanical clamping of the stem 452 by the wall of the recess 480.

A first component C of this adhesive (shown in FIG. 7) comprising ultra-accelerators and vulcanization activators is deposited on the means 450 by soaking the latter in a solution based on this first component, or by depositing a film of this first component on the stem 452 and on the head 451 by a method of the coextrusion type. This first component C covers the cylindrical surface of the stem 452 and the adjacent surface, in the form of a circular ring, of the head 451.

A second component of this adhesive (not shown) in the form of a solution comprising sulphur is deposited at the time of insertion of the means 490 in the form of a needle in the recess 480, on the external wall of the means 490, on the wall of the recess 480 and on the internal layer 420a of the tire 420 to which the head 451 is intended to be applied. The solution based on this second component facilitates the passage of the insertion means 490 in the recess 480, by lubrication.

After the insertion means 490 has been extracted from the tire 420, the first C and second components of the adhesive come in contact with each other and interact. It should be noted that this interaction is all the more effective, the greater the degree of mechanical clamping of the stem 452 by the wall of the recess 480.

It should also be noted that the bonding of the head 451 to the internal layer 420a of the tire 420 holds the means 450 against the wall of the recess 480 without the necessity of mechanical clamping of the stem 452 by the wall 480.

The adhesive used for fixing the stem 452 to the wall of the recess 480 is sold by the company Schrader under the name "Saphir", and is based on natural rubber and carbon black.

According to a variant embodiment (not shown), the transmission means 450 comprises the head 451 and the aforementioned translucent rubber composition part 453 only, which may be introduced and held in the recess 480 in the tire 420 according to the aforementioned methods.

It should be noted that an entirely translucent transmission means improves the precision of positioning of the wear detection threshold in the tire 420 with respect to the internal layer 420a thereof under which the head of the transmission means is applied. This is because the end of the stem of the means is adjusted after insertion of the latter in the recess 480 (the head then being applied under the internal layer 420a), so as to exactly position this end at the wear threshold to be detected using the tread pattern bottom as the reference surface.

The remaining volume of the recess 480 is entirely filled in with an opaque rubber composition like that of the tread, or with an opaque rubber cylinder which is deposited on the surface of this translucent stem.

Figure 10:
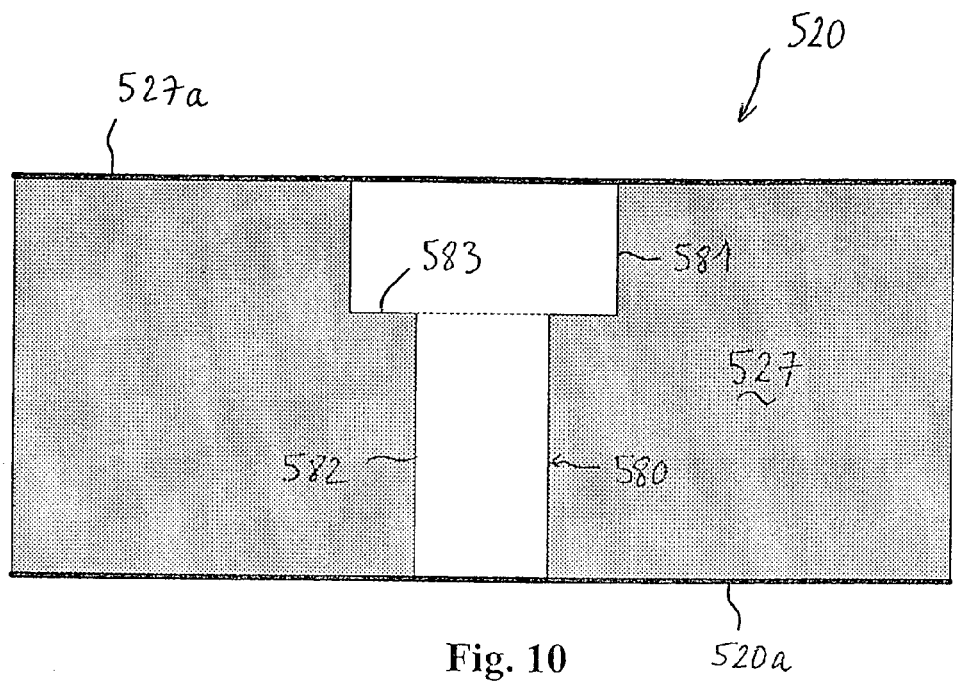
FIG. 10 is a schematic view in meridian section of portion of a tire in which there has been formed, through the radially external face of the tire and during the curing thereof, a recess intended to allow the introduction into the tire of a transmission means according to the invention.
Figure 11:
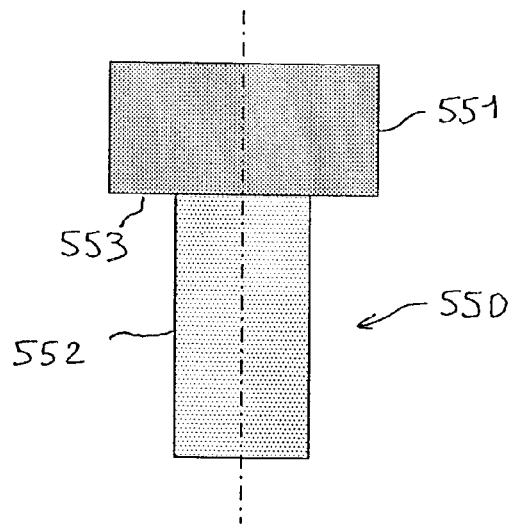
FIG. 11 is a view in axial section of a transmission means according to another example embodiment of the invention which is intended to be introduced into the tire of FIG. 10 through the radially external face.

FIG. 10 shows a tire 520 in which there has been formed, through the radially external face 527a thereof (forming the top of the corresponding tread pattern element 527) and during curing thereof, a recess 580 according to another embodiment of the invention which is intended to allow the insertion in the tire 520 of another transmission means 550 according to the invention (depicted in FIG. 11).

This recess 580 was formed from the external face 527a and extends as far as the internal face 520a of the tire 520. The recess 580 also has a symmetry of revolution but consists of a first cylindrical portion 581 of reduced height opening out on the external face 527a and a second concentric cylindrical portion 582 of greater height but lesser diameter, which opens out on the internal face 520a and which is connected to the first by a shoulder 583 corresponding to the wear threshold to be detected.

The diameter of the first portion 581 is, for example, 5 mm, whilst the diameter of the second portion 582 is, for example, 2.5 mm.

FIG. 11 illustrates the structure of this other transmission means 550 according to the invention which is intended to be inserted in the recess 580 of FIG. 10, this means 550 consequently comprising first portion 551 and second portion 552 and including a shoulder 553.

The second portion 552 of the means 550 is formed by a translucent rubber composition such as the one mentioned above with reference to FIG. 7, and the first portion 551 is formed by an opaque rubber cylinder (this rubber being, for example, identical to the one forming the tread) which is introduced radially outside the tire 520 in the recess 580.

Figure 12:
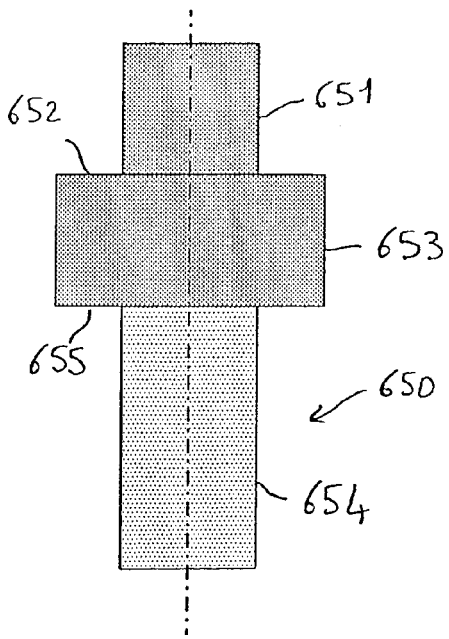
FIG. 12 is a view in axial section of a transmission means according to a variant embodiment of FIG. 11, also intended to be introduced into the tire of FIG. 10 through the radially external face.

FIG. 12 illustrates the structure of a variant embodiment according to the invention of this transmission means 650 (the recess intended to receive it not being shown, but being understood to have a similar profile).

As can be seen in FIG. 12, this means 650 comprises, from the external face to the internal face of the tire intended to receive it, a first cylindrical portion 651 which is formed from the opaque rubber composition and which is connected by a first shoulder 652 to a second concentric cylindrical portion 653 also formed from the opaque composition but with a diameter greater than the first portion 651, and a third cylindrical portion 654 concentric with the previous ones, which is formed from the translucent rubber composition and which is connected to the second portion 653 by a second shoulder 655.

It should be noted that the transmission means 550, 650 of FIG. 11 or 12 associated with the recess 580 of FIG. 10 allows the precise adjustment of the interface 553 between the translucent and opaque compositions at the shoulder 583 (or the second shoulder 655, in the example in FIG. 12), which corresponds to the wear threshold to be detected and is itself exactly positioned with respect to the tread pattern bottom, since it issues directly from the molding.

For the insertion and holding in the corresponding recesses of the transmission means 550, 650 according to FIG. 11 or 12, it is also possible to use (separately or in combination) the above described methods of mechanical clamping of the means by the wall of the recess 580 or of adhesive bonding via the adhesive of the two-component type.

In general terms, the recesses 480, 580 mentioned above in relation to FIGS. 9 and 10 were produced according to two distinct methods and via distinct piercing means, as indicated below.

Figure 13:
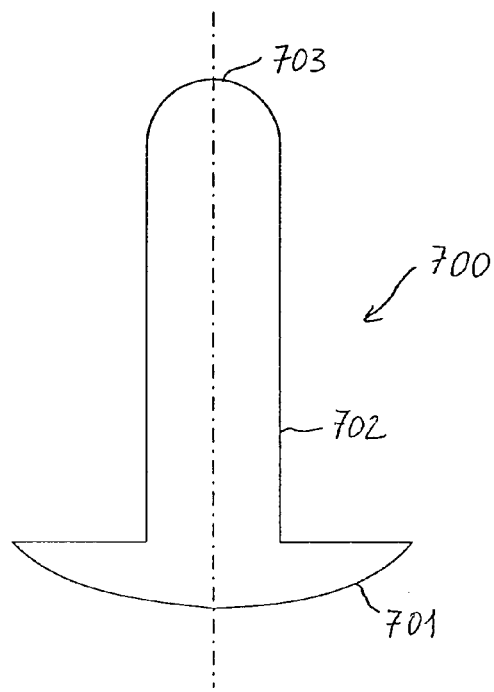
FIG. 13 is a view in axial section of an example of means according to the invention for producing a recess in a tire through its radially external face before the curing of the tire.

According to a first method used, applicable to the recesses 480 in FIG. 9, before curing of the outer tire casing, one or more metallic piercing means 700 are used, such as the one depicted in FIG. 13, which has in this example a symmetry of revolution, the cutting plane in question here containing the axis of symmetry of the means 700.

This piercing means 700 has substantially the shape of a thumb tack, comprising a head 701 having a rounded cap shape of slight thickness, which is provided with a cylindrical stem 702 at its center which is the diameter of the recess 480 to be produced and whose free end 703 is also shaped as rounded cap. This means piercing 700 is intended to be introduced into the outer casing 420 through the radially external face 427a of its tread. The length of this stem 702 is designed to be greater than the distance separating the internal layer 420a of the tire 420 from the radially uppermost surface of the last reinforcement of the crown reinforcement which the tire 420 has.

The piercing means 700 is advantageously formed from a metal covered with a low friction coating, for example, Teflon® brand coating material, and has for example a total height varying from 6 mm to 10 mm, the head 701 having a diameter varying from 20 mm to 40 mm and the stem 702 having a diameter varying from 1 mm to 5 mm.

The piercing means 700 may be introduced into the casing 420 at the desired location or locations for the recess or recesses 480. The casing is then cured and is positioned in the curing press (not shown) so as to place the piercing means 700 in the tread pattern element or elements of the mold which correspond to the one or ones 427 chosen to be provided with the transmission means 450.

After curing, this piercing means 700 are withdrawn from the tire 420 and in this way a passage 480 is formed through the cable plies of the tire 420, such as the working crown plies. The rubber remaining radially inside these plies is then perforated in order to ensure that the recess 480 opens out on the internal layer 420a of the tire 420.

Figure 14:
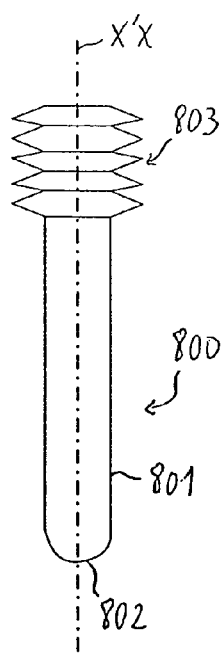
FIG. 14 is a schematic view in axial section of another example of means according to the invention for producing a recess which is adjustable for depth in a tire through its radially external face during the curing of the tire.
Figure 15:
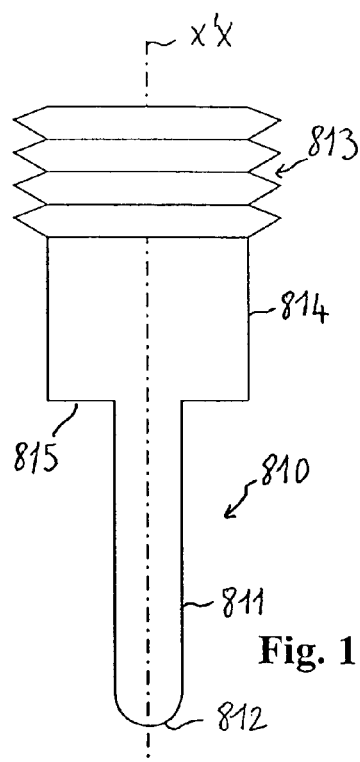
FIG. 15 is a schematic view in axial section of a variant of FIG. 14 of means according to the invention for producing a recess adjustable for depth in a tire through its radially external face during the curing of the tire.
Figure 16:
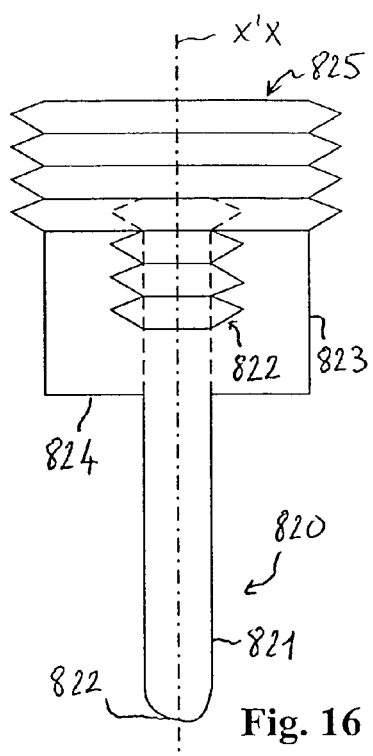
FIG. 16 is a schematic view in axial section of another variant of FIG. 14 of means according to the invention for producing a recess adjustable for depth in a tire through its radially external face during the curing of the tire.

According to a second embodiment of the recesses 480, 580 used during the curing of the casing (this method is applicable to the recesses 480 and 580 in FIGS. 9 and 10), the casing 420, 520 to be cured is placed in a curing mold provided with one or more metallic piercing means 800, 810, 820 like the ones depicted in FIGS. 14, 15 or 16. These piercing means 800, 810, and 820 have diameters corresponding to those of the recess or recesses 480, 580 to be produced, which, in turn, correspond to those for the transmission means 450, 550. Then, before curing, the casing 420, 520 is pierced by piercing means 800, 810, 820, and the piercing means are held in the casing 420, 520 during curing to keep in the separated position the cables of the various plies through which the piercing means 800, 810, 820 pass, without cables being cut or damaged.

The piercing means 800 shown in FIG. 14 comprises a cylindrical stem 801 the free end of which is for example in a shape of a rounded cap and which is provided with a means 803 of controlling its position along its axis of symmetry X'X. In the example in FIG. 14, this control means 803 is screw threads (i.e. a transmission screw).

The piercing means 810 shown in FIG. 15 comprises a cylindrical stem 811 such as the one in FIG. 14 which is connected to a means 813 of controlling its position along its axis of symmetry X'X, by means of a concentric portion 814 forming a shoulder 815 intended to constitute the wear threshold. In the example in FIG. 14, this control means 813 is also a transmission screw.

The piercing means 820 in FIG. 16 comprises a cylindrical stem 821 as mentioned previously which is provided with a screw 822 controlling its translation on the axis X'X, this screw 822 being mounted inside a concentric portion 823 which forms a shoulder 824 with the stem 821 and which is itself adjustable in translation via another control screw 825.

It should be noted that this shoulder 824 is designed to determine the wear threshold to be detected in the tread pattern element 527 in question.

With reference to the examples shown in FIGS. 14 to 16, it should also be noted that the stem 801, 811, 821 of each piercing means 800, 810, 820 has a diameter between 1 mm to 3 mm, and a length between from about 10 to 20 mm.

In addition, it should be noted that the slightly rounded shape of the free end 802, 812, 822 of each piercing means is designed so as to allow the formation of a recess 480, 580 in the cable plies without these cables being pushed radially or cut.

It should also be noted that the length of the piercing means 800, 810, 820 according to this second method is chosen so as to obtain a recess 480, 580 opening out in the radially internal layer 420a, 520a of the tire 420, 520, without piercing the curing membrane.

Thus there is formed in the cured tire 420, 520 a passage with a predetermined diameter through the cable plies without damaging the latter, particularly with regard to the crown plies. This method of producing the recesses 480, 580 during curing makes it possible in particular to subsequently introduce transmission means 450, 550 having a diameter greater than the pitch of the cables in the crown plies.

Figure 17:
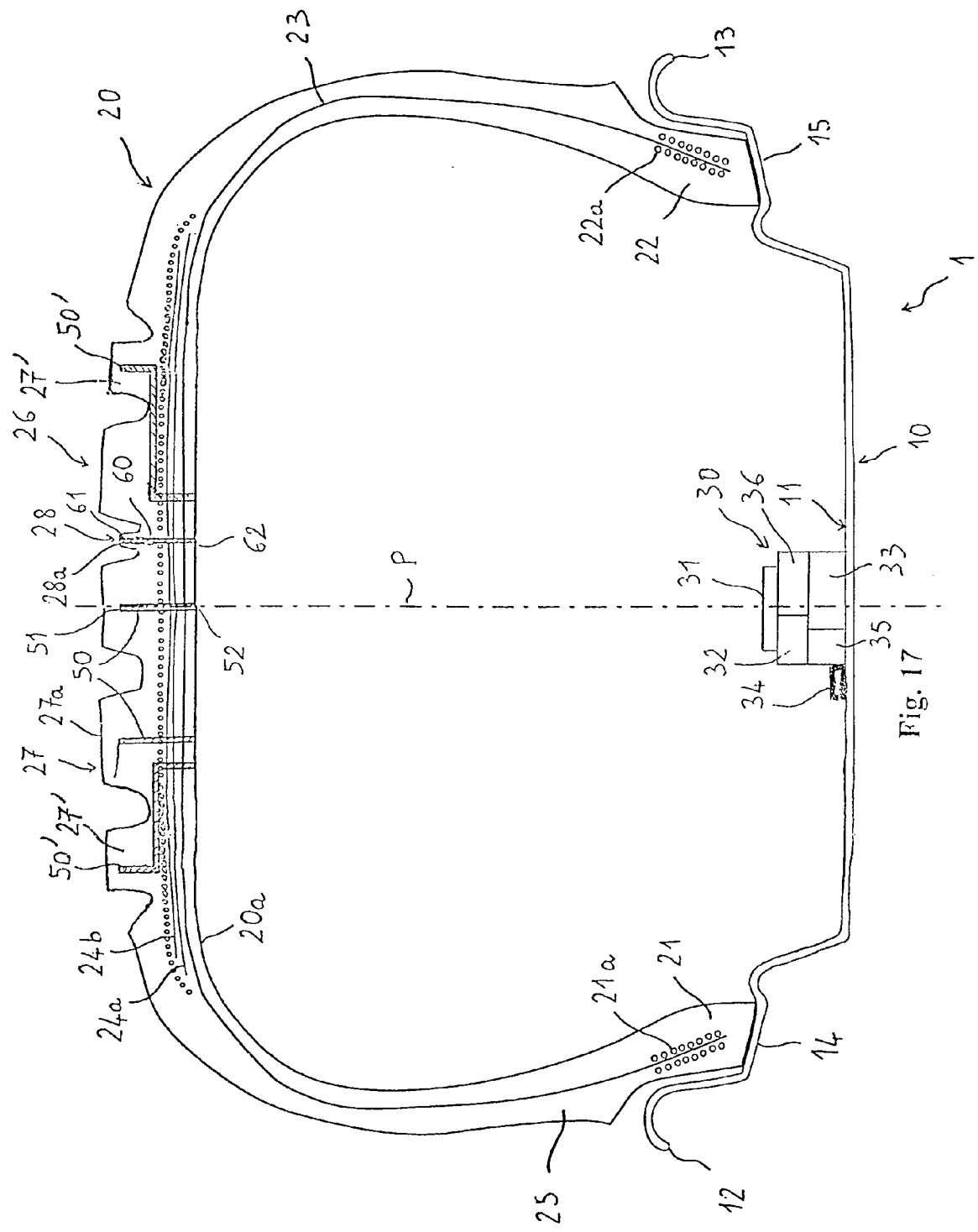
FIG. 17 is a schematic view in meridian section of a tire/wheel assembly according to the invention in accordance with a variant embodiment of FIG. 1, in which several radiation transmission means each comprise assemblies of non-rectilinear optical fibers; and, FIG. 18 is a schematic view in partial section along the circumferential mid-plane of FIG. 1 of a wheel rim according to a variant embodiment of the invention which is provided with a wheel module according to the invention comprising in particular the radiation detection means and means for concentrating the radiation towards the detection means.

FIG. 17 is a schematic view in meridian section of a tire/wheel assembly 1 according to the invention in accordance with a variant embodiment of FIG. 1, in which several radiation transmission means 50, 50', 60 each comprise assemblies of optical fibers with a diameter of between 50 µm and 100 µm which are embedded in a rubber sheath (not shown for reasons of clarity) in order to decouple them mechanically from the adjacent tread composition.

Each assembly illustrated in FIG. 17 is of the same type as those used for producing the metallic or textile cables in tires (i.e. twisted cables or layered cables with a finite or infinite winding pitch), and has increased resistance to the breakage caused by the deformations in running of the crown of the tire 20. It is, for example, possible to use assemblies each comprising around ten to a hundred optical fibers.

It should be noted that each of these assemblies can be introduced into the tire 20 after it is cured without prior piercing of the tire 20, by inserting through the radially external face 20a of the tire 20 a needle of the "medical needle" type, because of the reduced diameter of each assembly which allows its passage between the cables of the crown plies without imposing any significant local deformation on these cables.

This type of introduction allows the use of any tire, without prior discrimination between the tires 20 provided with transmission means 50, 50', 60 according to the invention and tires working normally.

As can be seen in FIG. 17, one or more assemblies of optical fibers 50, 50', 60 are installed in tire with the respective radially uppermost ends 51, 61 disposed in tread pattern elements 27' off center with respect to the circumferential mid-plane P of the tire/wheel assembly 1. Radiation detection means 30 is centered with the circumferential mid-plane P. The assemblies of optical fibers 50' can be non-rectilinear overall (i.e. consisting of a succession of rectilinear segments connected together by elbows), so that the radially lower end 52 of each assembly which is intended to transmit the radiation to the radiation detection means 30 opens out on the radially internal face 20a of the tire 20 whilst being practically opposite the detection means 30.

It should be noted that this non-rectilinear geometry for the assembly of optical fibers makes it possible to dissociate the positioning of the upstream end 51 (for example situated in the "shoulder" area of the tire 20 of each transmission means 50', from the positioning of the remaining part of the means 50' which passes at right angles through the cable plies, without any risk of degrading the functioning of these cables, by positioning the passage of the transmission means 50' in line with these cables at the least detrimental locations, for example at one third of the width of the tread.

Figure 18:
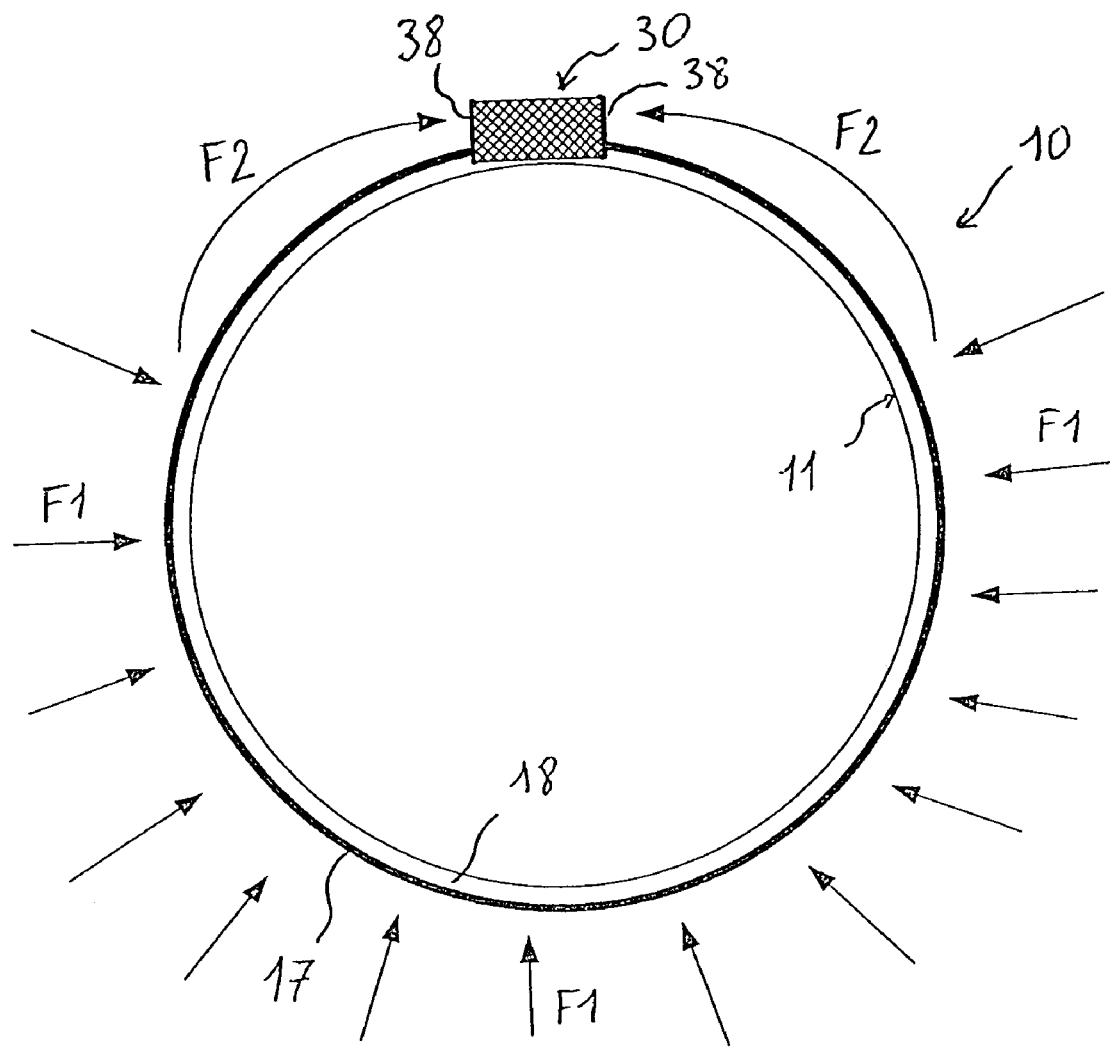

FIG. 18 is a schematic view in partial section along the circumferential mid-plane P of FIG. 1 of a rim 11 of a wheel 10 according to a variant embodiment of the invention. The rim 11 is provided with a wheel module 30 according to the invention comprising, in particular, means of detecting the radiation transmitted by a transmission means according to the invention (the detection means and the transmission means not being shown), and means 17 for picking up and concentrating this radiation towards the detection means.

The rim 11 shown in FIG. 18 has a "collar" 18 for holding the wheel module 30, which is for example as defined in relation to FIG. 1. This holding collar 18 in a known manner matches the cylindrical geometry of the rim 11. According to one example embodiment of the invention, the collar 18 comprises, on its radially outermost face, means 17 for picking up the radiation received on its surface in radial directions (see arrows F1) with respect to the cylindrical surface of the rim 11 and for concentrating this picked-up radiation by directing it practically along the cylindrical surface of the rim 11 (see arrows F2) towards at least one surface 38 of the wheel module 30 containing the radiation detector.

It should be noted that the means 17 for picking up and concentrating the radiation can be formed using the material or materials precisely constituting the holding collar 18 and that it can thus advantageously have a reduced cost per unit surface area.

This dissociation of the means 17 for picking up the radiation and the wheel module 30 makes it possible not to have to carry out a precise "azimuthing" of the transmission means with respect to the radiation detection means (i.e. ensuring that the transmitted radiation detection means is situated precisely opposite the or each transmission means or at least in the "cone" of the radiation transmitted by the latter).

With reference to any one of the embodiments in FIGS. 1, 2, 5 or 18, the method according to the invention for measuring the wear on a tire 20, 120, 220 comprises the following steps. Non-limitingly, it will be considered below for reasons of clarity of the disclosure that the incident radiation external to the tire 20, 120, 220 consists of visible light.

As long as the wear on one of the tread pattern elements 27, 127, 227 of the tire 20, 120, 220 has not reached the perimeter or the radially uppermost upstream surface 51, 151, 251 of the light transmission means 50, 150, 250 situated in the tread pattern element, this transmission means does not open out on the top 27a, 127a, 227a of the tread pattern element. As a result, the detection means 31 does not detect transmitted light in the space internal to the tire 20, 120, 220, which results in the fact that the radio receiver 41 mounted on the vehicle 40 receives no light signal from the transmitter 33. Consequently the display 44 signals no alert information to the driver of the vehicle 40 concerning wear on the tire 20, 120, 220.

After the wear on a tread pattern element 27, 127, 227 has reached the perimeter or the radially outermost surface 51, 151, 251 of the corresponding light transmission means 50, 150, 250, the transmission means is uncovered and opens on the surface of the tread element top 27a, 127a, 227a. The transmission means now transmits, to the space internal to the tire 20, 120, 220, light coming from outside the tire, and this transmitted light is detected by the detection means 31. The transmitter 33 then transmits a signal representing the detected light to the receiver 41 via the antenna 34, and the driver is informed by the display 44 that a wear threshold has been reached for the tread pattern element 27, 127, 227 (critical or not, according to the predetermined height initially separating the transmission means 50, 150, 250 from the top 27a, 127a, 227a of the tread pattern element).

In the example in FIG. 2 where the radially outermost part 153 has a cross-section increasing in the direction radially opposite to the top 127a of the tread pattern element 127, it should be noted that the accentuation of the wear on the tread pattern results in a continuous increase in the quantity of transmitted light which is detected by the detection and quantification means 31, and therefore in the signal representing this detected quantity which is received by the receiver 41 and, consequently, delivered continuously in the form of alert messages to the driver of the vehicle 40.

In the case of a light transmission means 60 which is situated in a "wear indicator" or wear bar 28, it should be noted that there is practically zero initial distance separating the radially outermost end 61 of this transmission means 60 from the top 28a of the wear bar 28. This small distance leads to the result that, when the wear on the tire 20 is such that the wear bar 28 makes wear contact with the ground, the transmission means 60a little time afterwards is flush with the surface of the top 28a and then transmits the external light to the internal space of the tire 20. The result is the detection of this light and the transmission to the receiver 41 of a representative signal which is delivered to the driver of the vehicle 40 in the form of an alert message signifying that the wear threshold has been exceeded.

It should be noted that the embodiment in FIG. 5 is particularly advantageous, since it takes account of an average wear over the entire circumference of the tire 220, with consequently increased reliability for the detection of the fact that the light transmission means 250 is flush with the circumference.

With reference to the embodiment in FIGS. 3 and 4, the method according to the invention for measuring the wear on a tire 320 is differentiated from what has just been stated solely in that the detection means 331 can detect several stages of wear via a single light transmission means 350, because the latter contains a plurality of measuring optical fibers 373 to 378 which, as the tire wears, become successively flush with the surface of the top 327a of the tread pattern element 327.

In conclusion, it should be noted that provision could also be made for installing a radio receiver on a terminal fixed to the ground (instead of the receiver 41 mounted on the vehicle 40) placed in a route where the vehicle 40 passes.

It should also be noted that the display 44 could serve as an interface vis-à-vis users other than solely the driver of the vehicle 40.

What is claimed is:

1. A method of measuring the wear on a tire mounted on a wheel, the tire comprising tread pattern elements and defining an internal space, the method comprising the steps of detecting at a location within the internal space electromagnetic radiation transmitted through at least one tread pattern element from outside the tire, determining an energy variable from the detected electromagnetic radiation, and determining a wear variable representative of wear on the at least one tread pattern element from the energy variable.

2. A method of measuring the wear on a tire according to claim 1, wherein the at least one tread pattern element has a top surface for contact with the ground, and wherein electromagnetic energy is transmitted through a transmitter element communicating with the top surface of the at least one tread pattern element, the energy variable being representative of a height of the at least one tread pattern element.

3. A method of measuring the wear on a tire according to claim 1, wherein the method comprises the step of comparing the value of the energy variable to a predetermined energy threshold, wherein, a value of the energy variable less than the predetermined energy threshold corresponds to a value of the wear variable less than a predetermined wear threshold.

4. A method of measuring the wear on a tire according to claim 1, wherein the method comprises the step of comparing the value of the energy variable to a predetermined energy threshold, wherein a value of the energy variable equal to or greater than the predetermined energy threshold corresponds to a value of the wear variable at or above a predetermined wear threshold.

5. A method of measuring the wear on a tire according to claim 4, wherein the method comprises the step of comparing the value of the energy variable to a plurality of energy values equal to or greater than the predetermined energy threshold, wherein the energy values correspond to levels of wear on the tread pattern element from the predetermined wear threshold to a maximum wear level, and wherein wear on the element is measured continuously between the wear threshold and the maximum wear level.

6. A method of measuring the wear on a tire according to claim 1, wherein the electromagnetic radiation transmitted through the at least one tread pattern element consists of visible light.

7. A tire having an internal space defined by a radially inner face and having tread pattern elements for ground contact, the tire comprising an electromagnetic radiation transmitter element embedded in at least one tread pattern element and operable to transmit through the at least one tread pattern element incident electromagnetic radiation issuing externally of the tire to the internal space when a radially outer portion of said transmitter element is flush with a top surface of the at least one tread pattern element.

8. The tire according to claim 7, wherein the transmitter element is permeable to visible light.

9. The tire according to claim 7, wherein the tire comprises a plurality of electromagnetic radiation transmitter elements which have respectively various colors in the spectrum of the visible range.

10. The tire according to claim 7, wherein said transmitter element has a cross-section in the axial direction of the tire whose area increases continuously from radially outward toward radially inside said tire, wherein as the at least one tread pattern element wears, an exposed area of the cross-section of the transmitter element at the top surface of the at least one tread pattern element increases, wherein a quantity of radiation energy transmitted to the internal space increases continuously.

11. The tire according to claim 7, wherein said transmitter element extends over an entire circumference of the tire.

12. The tire according to claim 7, wherein the tire comprises a plurality of electromagnetic radiation transmitter elements having respective heights, measured in the radial direction of the tire, which heights correspond to various predetermined wear thresholds to be detected for the tread pattern element.

13. The tire according to claim 7, wherein said radiation transmitter element comprises at least one optical fiber communicating with the internal space.

14. The tire according to claim 13, wherein said radiation transmitter element comprises an assembly of optical fibers of the twisted cable or layered cable type which is embedded in a rubber composition which mechanically decouples the assembly from adjacent rubber compositions in the tire.

15. The tire according to claim 13, wherein the transmitter element comprises at least two optical fibers disposed in parallel extending into a radially uppermost part of the tire through the radially inner face and each terminating at a selected radial height in a respective one of the tread pattern elements recessed from its top, the radial height of each fiber termination corresponding to a predetermined wear threshold, and, further comprising a radiation detector disposed in the internal space of the tire, said detector operably connected to the at least two optical fibers for detecting the energy of the radiation which is transmitted thereto by the at least two optical fibers.

16. The tire according to claim 15, wherein the detector further comprises a signal transmitter coupled to an antenna for transmitting electrical signals representing radiated energy measurements and a microprocessor for processing the radiated energy measurements.

17. The tire according to claim 7, wherein said transmitter element comprises at least one rubber composition which is based on at least one elastomer and which has a modulus of elasticity MA10 (at 10% deformation), measured in accordance with ASTM D 412 of 1998, which is between 1 MPa and 20 MPa.

18. The tire according to claim 17, wherein the elastomer belongs to the family comprising cross-likable elastomers with sulphur or with peroxides, thermoplastic elastomers, true polyurethanes and derivatives of polyurethanes, such as polyurethane/urea, polyureas, polyurealurethane, polyurethane/isocyanurate, polyurealisocyanurate and polyurethane/urealisocyanurate.

19. The tire according to claim 17, wherein the elastomer belongs to the family comprising polyisoprenes, styrene/butadiene copolymers, isoprene/styrene copolymers and polybutadienes.

20. The tire according to claim 7, wherein said transmitter element comprises at least one translucent rubber composition comprising an elastomer, a paraffin oil by way of plasticizer, at least one non-staining phenolic antioxidant as an antioxidant and a reinforcing inorganic filler as a reinforcing filler, said translucent composition containing no carbon black.

21. The tire according to claim 7, wherein said transmitter element is based on at least one material having a modulus of elasticity MA10 (at 10% deformation), measured in accordance with ASTM D 412 of 1998, which is between 1 GPa and 10 GPa.

22. The tire according to claim 21, wherein the material is based on glass, a thermoplastic polymer such as a polystyrene, a methyl polymethacrylate, a polycarbonate, a polyamide, a polyvinyl chloride or a polyester, or a thermosetting polymer.

23. The tire according to claim 7, wherein said transmitter element comprises at least one optical fiber formed from a core based on glass, silica or quartz and a sheath based on a thermoplastic polymer or a glass, a silica or a quartz with a refractive index less than that of the core.

24. The tire according to claim 7, wherein said transmitter element comprises at least one optical fiber formed from a core based on a plastics material and a sheath based on another plastics material with a refractive index less than that of the core.

25. The tire according to claim 24, wherein said transmitter element comprises a core which is based on the material or materials and which is intended to transmit the radiation, and a sheath based on a cellular rubber which encloses the core and which is designed to decouple it mechanically from the adjacent rubber compositions in the tire.

26. The tire according to claim 25, wherein the sheath is based on cellular rubber with closed cells and has a modulus of elasticity MA10, measured in accordance with ASTM D 412 of 1998, of between 0.1 MPa and 1 MPa.

27. The tire according to claim 7, wherein said transmitter element is inserted in the tire following the curing of the corresponding outer casing.

28. The tire according to claim 7, wherein said transmitter element comprises a head and a stem extending from a center of the head, the stem being contained in a radially directed recess formed from the internal face toward the top of a respective tread pattern element, the head being in contact with the internal face and a free end of the stem being at the surface of the top, the head and a first part of the stem extending from the head being formed from a translucent rubber composition and a second part of the stem including the free end being formed from at least one opaque rubber composition, an interface between the translucent composition and the opaque composition being positioned at a radial height selected to correspond to a wear threshold to be detected in the tread pattern element.

29. The tire according to claim 7 further including an electromagnetic radiation detector carried by the tire within the internal space.

30. A wheel having a rim configured to mount a tire having electromagnetic radiation transmission means to transmit through at least one tread pattern element of the tire incident radiation from externally of the tire to an internal space formed with the tire mounted on the wheel, and an electromagnetic radiation detector mounted on the rim and arranged for detecting energy of electromagnetic radiation transmitted radially into the tire from outside of the tire for measuring tread wear.

31. The wheel according to claim 30, further comprising means for quantifying the energy of the radiation transmitted to the internal space.

32. The wheel according to claim 30, further comprising means for discriminating visible radiation by color transmitted into the internal space.

33. The wheel according to claim 30, wherein said detector is contained in a wheel module which is mounted on the rim and which further comprises means to monitor the operating parameters of the tire/wheel assembly, the wheel module also comprising a signal transmitter coupled to an antenna for transmitting electrical signals representing measurements of radiated energy, temperature and pressure, and a microprocessor intended to process the measurements of radiated energy, temperature and pressure.

34. The wheel according to claim 30, further comprising means for receiving radiation transmitted to a surface of the rim in radial directions with respect to the rim surface and for concentrating received radiation by directing it along the rim surface toward said detector.

35. The wheel according to claim 34, further comprising a collar for holding the wheel module provided at a bottom of a rim of the wheel, a radially uppermost face of the collar comprising the means for receiving and concentrating the radiation.

36. The tire according to claim 30 wherein the detector further includes a signal transmitter for emitting signals representing measurements of detected electromagnetic radiation energy.

37. A tire/wheel assembly comprising:
a tire having an internal space defined by a radially inner face and having tread pattern elements for ground contact, the tire comprising an electromagnetic radiation transmitter element to transmit through at least one tread pattern element incident radiation issuing externally of the tire when said transmitter element is made flush with a top surface of the at least one tread pattern element in response to tread wear,
a wheel, the tire being mounted on the wheel and defining an internal space between the tire and the wheel, and
a radiation detector disposed in the internal space for detecting energy of radiation transmitted to the internal space by said transmitter element through the at least one tread pattern element.

38. The tire/wheel assembly according to claim 37 wherein the detector further includes a signal transmitter for emitting signals representing measurements of detected electromagnetic radiation energy.

39. A motor vehicle, having at least one tire/wheel assembly,
the tire/wheel assembly comprising a tire having an internal space defined by a radially inner face and having tread pattern elements for ground contact, the tire comprising an electromagnetic radiation transmitter element to transmit through at least one tread pattern element incident radiation issuing externally of the tire, when said transmitter element after wear is made flush with a top surface of the at least one tread pattern element,
a wheel, the tire being mounted on the wheel and defining an internal space between the tire and wheel, and,
a radiation detector disposed in the internal space for detecting energy of radiation transmitted to the internal space by said transmitter element through the at least one tread pattern element, and generating a signal representative of said detected radiation, and a signal transmitter for transmitting said signal externally of the wheel;
the vehicle further comprising a receiver to receive signals from the signal transmitter, a computer connected to the receiver to process the signals, and a display installed in the cabin of the vehicle connected to the computer and configured to inform a vehicle operator of a state of wear of the tread pattern elements of the tire of the at least one tire/wheel assembly.

40. The vehicle according to claim 39 wherein the detector further includes a signal transmitter for emitting signals representing measurements of detected electromagnetic radiation energy.

\* \* \* \* \*